(12) United States Patent
Duncan

(10) Patent No.: US 7,851,595 B2
(45) Date of Patent: Dec. 14, 2010

(54) MEMBRANE FUSION PROTEINS DERIVED FROM REOVIRUS

(75) Inventor: Roy Duncan, Dartmouth (CA)

(73) Assignee: Innovascreen Inc., Halifax, CA (US)

( * ) Notice: Subject to any disclaimer, the term of this patent is extended or adjusted under 35 U.S.C. 154(b) by 0 days.

(21) Appl. No.: 11/952,714

(22) Filed: Dec. 7, 2007

(65) Prior Publication Data
US 2008/0124793 A1    May 29, 2008

Related U.S. Application Data

(63) Continuation of application No. 10/433,276, filed on Jun. 2, 2003, now abandoned.

(51) Int. Cl.
*C07K 14/00* (2006.01)
*C12N 1/21* (2006.01)

(52) U.S. Cl. ..................... 530/350; 424/215.1

(58) Field of Classification Search ........................ None
See application file for complete search history.

(56) References Cited

U.S. PATENT DOCUMENTS 5,948,889 A * 9/1999 de Boer et al. .............. 530/350

OTHER PUBLICATIONS

Sheng H. et al., Synthesis in *Escherichia coli* of Avian reovirus Core Protein qA and its dsRNA-binding activity. (2002) Virology 266, pp. 33-41.*
Top et al. (PLOS Pathogens 2009, vol. 5, p. 1-14.*
Clancy, Journal of Virology, 2009, vol. 83, p. 2941-2950.*
Attwood et al, The Babel of bioinformatics. Science (2000) vol. 290, No. 5491, PDF having pp. 1-7).*
Shmulevitz et al. (The EMBO Journal, vol. 19, p. 902-912.*

* cited by examiner

*Primary Examiner*—Zachariah Lucas
*Assistant Examiner*—Agnieszka Boesen
(74) *Attorney, Agent, or Firm*—Gowling LaFleur Henderson LLP

(57) ABSTRACT

In accordance with the present invention, a family of membrane fusion protein and polynucleotides encoding the proteins have been identified. The proteins and nucleotides are derived from the family Reoviridae. Two membrane fusion proteins have been isolated from reoviruses isolated from poikilothermic hosts: the p14 protein from reptilian reovirus (RRV) isolated from python, and the p16 protein from aquareovirus (AQV) isolated from salmon. The genes encoding these proteins have been cloned and sequenced. Analysis of the amino acid sequences of these proteins show that both lack the typical fusion peptide motif found in other membrane fusion proteins. Expression of these proteins in cells results in cell-cell fusion.

1 Claim, 10 Drawing Sheets

FIGURE 2: RRV S1 Genome Segment Encoding the p14 and sigma C
Proteins

```
GTTATTTTTTTCCTCGATGAAGCCATGGGAGTGGACCCTCTAATTTCGTCAATCACGCA    60
                    p14  M  G  S  G  P  S  N  F  V  N  H  A   12

CCTGGAGAAGCAATTGTAACCGGTTTGGAGAAAGGGGCAGATAAAGTAGCTGGAACGATA  120
 P  G  E  A  I  V  T  G  L  E  K  G  A  D  K  V  A  G  T  I   32

TCACATACGATTTGGGAAGTGATCGCCGGATTAGTAGCCTTGCTGACATTCTTAGCGTTT  180
 S  H  T  I  W  E  V  I  A  G  L  V  A  L  L  T  F  L  A  F   52

GGCTTCTGGTTGTTCAAGTATCTCCAAAAGAGAAGAGAAAGAAGGAGACAACTCACTGAG  240
 G  F  W  L  F  K  Y  L  Q  K  R  R  E  R  R  R  Q  L  T  E   72

TTCCAAAAACGGTATCTACGGAATAGCTACAGGTTGAGTGAGATCCAGAGACCTATATCA  300
 F  Q  K  R  Y  L  R  N  S  Y  R  L  S  E  I  Q  R  P  I  S   92

CAGCACGAATACGAAGACCCATACGAGCCACCAAGTCGTAGGAAACCACCCCCTCCTCCT  360
 Q  H  E  Y  E  D  P  Y  E  P  P  S  R  R  K  P  P  P  P  P  112

TATAGCACATACGTCAACATCGATAATGTCTCAGCCATTTAGTGATGAGCAACGGAGGGC  420
 Y  S  T  Y  V  N  I  D  N  V  S  A  I  *                    125
                   sigma C  M  S  Q  P  F  S  D  E  Q  R  R  A  12

CATTATTAAGTTATGCTTGGCATTTGCTGACGGAGGAACATCAGGAGCCGATGTAGATGA  480
 I  I  K  L  C  L  A  F  A  D  G  G  T  S  G  A  D  V  D  E   32

GTTGATACGTCGCATGGCGGCATTAGAGGTATCGTTAGTAGAGATAAGGCGAGACCTGAC  540
 L  I  R  R  M  A  A  L  E  V  S  L  V  E  I  R  R  D  L  T   52
```

FIGURE 2: CONT'D

```
GGTTCTAGATGGGGATGTAGCCTCTGTAATCCGTAGACTACAGGACGCTGAGGACGCGAT  600
 V  L  D  G  D  V  A  S  V  I  R  R  L  Q  D  A  E  D  A  I   72

AACGGCATTGTCCAACGCGATGCAGGTGGTCCAATCACATATTGAAGAGATAGTTACGCA  660
 T  A  L  S  N  A  M  Q  V  V  Q  S  H  I  E  E  I  V  T  Q   92

AGTTCGAAAACAAGTGGAGCAGATAGCGGCTTTGGAGACGGCGGTGACTCAGAACACGAA  720
 V  R  K  Q  V  E  Q  I  A  A  L  E  T  A  V  T  Q  N  T  K  112

GGACATAGATAGTGTGCGTAGCACGGTAACGGATTTAGGATCCTTAGTGAGTGCAGAGAA  780
 D  I  D  S  V  R  S  T  V  T  D  L  G  S  L  V  S  A  E  K  132

AGTGAGGTTGGACGGTGTGGCGAGAGATGTGTCGACACAGGGACTGTCAATCACTGATTT  840
 V  R  L  D  G  V  A  R  D  V  S  T  Q  G  L  S  I  T  D  L  152

GCAGGCGCGAGTAGCTAAATTAGAAAGGGAAGCTGAACCGACGTCGTTCGAATGGCCACT  900
 Q  A  R  V  A  K  L  E  R  E  A  E  P  T  S  F  E  W  P  L  172

GAGAAAAGATGCGAAGAGTGGATTGCTATCATTGAACTGGGATCCTTGGTTCTTAGAAAC  960
 R  K  D  A  K  S  G  L  L  S  L  N  W  D  P  W  F  L  E  T  192

GACTGAAATATTTGGACTCTCATGGGCGCAGTCTGGAGTTGAGATGGGAGCCACAACTGG 1020
 T  E  I  F  G  L  S  W  A  Q  S  G  V  E  M  G  A  T  T  G  212

ACAAGGAGAATGGCATACACAAAGTGGTGATTACTTGTACACCGTGAGCCTTAACTTTAA 1080
 Q  G  E  W  H  T  Q  S  G  D  Y  L  Y  T  V  S  L  N  F  K  232

ATTCTACAGATACAGGTCTATGGGAGCCTTTTCACTCTCAACCGGGAATGCGTTGCTGAA 1140
 F  Y  R  Y  R  S  M  G  A  F  S  L  S  T  G  N  A  L  L  N  252
```

FIGURE 2: CONT'D

```
CGGCCCAAAGGTGGAGCTACGTATACCATATACCACAGGGGGACTGGCCTAGAAGGATC 1200
 G  P  K  V  E  L  R  I  P  Y  T  T  G  G  T  G  L  E  G  S   272

TGACCTACAAAACATGACGCCATCGTCCACCACGAGATTTCCGTTGACGTTCGTGACACG 1260
 D  L  Q  N  M  T  P  S  S  T  T  R  F  P  L  T  F  V  T  R   292

AATAACGGTAGGAGGAAGTGAATATACCATGCCAATTACGGTGACAATACGACGAATTAG 1320
 I  T  V  G  G  S  E  Y  T  M  P  I  T  V  T  I  R  R  I  S   312

TGGTGTGGATACAATCGTGCTAACTCCAGCGGATTTGCCAGGCGCCACAAGCTATCCATG 1380
 G  V  D  T  I  V  L  T  P  A  D  L  P  G  A  T  S  Y  P  C   332

TTATCTGAGGGGGGAGTCGATATTTTACTACATGAGGGCTAGGCAGATGACGTGATTGCG 1440
 Y  L  R  G  E  S  I  F  Y  Y  M  R  A  R  Q  M  T  *          349

TGAAGAGGGACTCTCCCCGTAAGGTGAAGCACGATGGGACGTGCGAGGAAAGCTATTCAT 1500

C                                                              1501
```

FIGURE 3: AQV Genome Segment 7 Encoding the p16 and NS28 Proteins

```
GTTTTAGTCAATCATCCTGGGGAATACCATCTCAAACACCGTTCAGTACACGGTACTGCA    60
  p16  S  I  I  L  G  N  T  I  S  N  T  V  Q  Y  T  V  L  Q    18

GATCGACAGATCTTGCTGTATCAAAACCAGCCTCACCGCCACTTCCGAAGCCACTTCCTG   120
   I  D  R  S  C  C  I  K  T  S  L  T  A  T  S  E  A  T  S  W   38

GGCCATCCCCCCTCTCGCAATCTGTTGCTGCTGTTGCATCTGCTGTACCGGCGGACTATA   180
   A  I  P  P  L  A  I  C  C  C  C  I  C  C  T  G  G  L  Y      58

TCTCGTTCATTCTGGACGTTTTCCAGGCCTCAGCCGAAGGTTGGACGTGCTCGGAGGTTC   240
   L  V  H  S  G  R  F  P  G  L  S  R  R  L  D  V  L  G  G  S   78

GGGGTCAACCCCAAAACACTCGCTGCGTAGCCACGGCACCCAAAGCCACGTGTACATCGC   300
   G  S  T  P  K  H  S  L  R  S  H  G  T  Q  S  H  V  Y  I  A   98

GTTAGCTTCAGTGATTCTAGTGACTCTAGTGATATCTCTGATCTGGAATTGCCTCGGCAC   360
   L  A  S  V  I  L  V  T  L  V  I  S  L  I  W  N  C  L  G  T  118

GGGTCTCATCCTCTGGCGCATTCATTCAGGCCTGAAGTCGATCGCCACCGCCCTCGTCCC   420
   G  L  I  L  W  R  I  H  S  G  L  K  S  I  A  T  A  L  V  P  138

TCAACGCAAGTCCAGCAGACATCTTTCATCCCGCTCGTACCACTCAGCTCCGGATCAAGT   480
   Q  R  K  S  S  R  H  L  S  S  R  S  Y  H  S  A  P  D  Q  V  158

TTAGACGATGGGATCGTACGCTCTCAACCCTCACGGGATTCGCGGCCCCACGAGCAATTT   540
    *
  NS28  M  G  S  Y  A  L  N  P  H  G  I  R  G  P  T  S  N  L    18
```

FIGURE 3: CONT'D

```
GAGGATTGGCTTCAACAAGCACATCTCCTACGACCAGGACGAGTTTCCGGATCTACCAAC  600
 R  I  G  F  N  K  H  I  S  Y  D  Q  D  E  F  P  D  L  P  T   38

CCCTTCACCTGACCACATTCCCGACTGGGTGACGGATCATGACAAGTTCAACGGTCATCC  660
 P  S  P  D  H  I  P  D  W  V  T  D  H  D  K  F  N  G  H  P   58

CCTCCCCCTCGTCTACGATGGACGTCTGACACCCATCACGGGTCCTCACCATCTTTGGGA  720
 L  P  L  V  Y  D  G  R  L  T  P  I  T  G  P  H  H  L  W  E   78

GCCTGACAGTTATGTAGAGTGGCAGACCTGGGGGTGCCTCCGACCCTTCTCTCCTTTCAG  780
 P  D  S  Y  V  E  W  Q  T  W  G  C  L  R  P  F  S  P  F  S   98

CGTTTGGCCACCAACGGTACCGAACTGGTTCAGCCGTAAGGTCCTCCACGTCTTCAGCAA  840
 V  W  P  P  T  V  P  N  W  F  S  R  K  V  L  H  V  F  S  N  118

CATGTCCCCGTACGCCTGCGCTGCTGAGAAGAGTCCCAATCCCCTTCCCTACTGGCGTTT  900
 M  S  P  Y  A  C  A  A  E  K  S  P  N  P  L  P  Y  W  R  L  138

GAATGATCAGGGTCGTGACTGGAGCGTATTCTGGGACTTAATTTGGCGATGTGCTCAGAC  960
 N  D  Q  G  R  D  W  S  V  F  W  D  L  I  W  R  C  A  Q  T  158

ACGTGGTGCTCGCATCTGTTTTGCGAAGACCCCCTTCATCCAGACGATGCTACGCCTGAC 1020
 R  G  A  R  I  C  F  A  K  T  P  F  I  Q  T  M  L  R  L  T  178

TGACGATCAGCTGTCCCGTCTTCCATCCGCTGAGGATCCAATCAGTCTCTTAAACATCGC 1080
 D  D  Q  L  S  R  L  P  S  A  E  D  P  I  S  L  L  N  I  A  198

AGGATGGGACGCCCTTCTTCTCAACGGTCTTCCCCCTAACCTGGTGCGAGCATTGATGAG 1140
 G  W  D  A  L  L  L  N  G  L  P  P  N  L  V  R  A  L  M  R  218
```

FIGURE 3: CONT'D

```
GTCCCCTCCAAACCCAGAGGTCGTTGAGCTGGATCTGCTCGTCTCCTGGTTCGATGTCGT 1200
 S   P   P   N   P   E   V   V   E   L   D   L   L   V   S   W   F   D   V   V    238

GATTCGTATTCCCTATGACGTGCAACACCCCCTAGGCCTTGGTTTCAGCCCTGATCAATT 1260
 I   R   I   P   Y   D   V   Q   H   P   L   G   L   G   F   S   P   D   Q   F    258

TTGGACTCATCCGTTCGTCGTCCTGTGCTACCTGCGCTGGCGTTTGTTGGGAGGTGACGA 1320
 W   T   H   P   F   V   V   L   C   Y   L   R   W   L   L   G   G   D   D    278

CTAGGATGGCGTCCGCGACAGTTGAGGCCTGGGCCTCGGGGATTTAGTCCCCTGTCGCCA 1380
 *

GCGTGACTGCTATTCATC                                            1398
```

Figure 4: Reptilian Reovirus p14 Membrane Fusion Protein Motifs

```
          myr                                    transmembrane
        ─────────                            ──────────────────── +   +++
1    MGSGPSNFVNHAPGEAIVTGLEKGADKVAGTISHTIWEVIAGLVALLTFLAFGFWLFKYLQKRRE pro
     +++      ++  +   +    +                 ─────
66   RRRQLTEFQKRYLRNSYRLSEIQRPISQHEYEDPYEPPSRRKPPPPPYSTYVNIDNVSAI
```

Figure 5: Aquareovirus p16 Membrane Fusion Protein Motifs

```
                                                        transmembrane
                                                    ───────────────────────   +
1    SIILGNTISNTVQYTVLQIDRSCCIKTSLTATSEATSWAIPPLAICCCCCICCTGGLYLVHSGRF transmembrane
         ++            ++   + +     +   ─────────────────────────── + +   +
66   PGLSRRLDVLGGSGSTPKHSLRSHGTQSHVYIALASVILVTLVISLIWNCLGTGLILWRIHSGLK

++  ++    +   +
131  SIATALVPQRKSSRHLSSRSYHSAPDQV
``` p10 MEMBRANE FUSION PROTEIN OF ARV

Ser
Cys
Asn—Gly
Ala
Thr
Ala—Ile—Phe
Gly
Asn
Val—His
Cys
Gln—Ala
Ala
Gln
Asn

FIG. 6A p10 MEMBRANE FUSION PROTEIN OF NBV

Asp
Cys
Ala—Lys
Ile
Val
Ser—Val
Phe
Gly—Ser
Val
His
Cys———Gln
Ser
Ser

FIG. 6B

SEQUENCE LISTING

```
<160> NUMBER OF SEQ ID NOS: 9

<210> SEQ ID NO 1
<211> LENGTH: 1501
<212> TYPE: DNA
<213> ORGANISM: reptilian reovirus
<220> FEATURE:
<221> NAME/KEY: CDS
<222> LOCATION: (25)..(402)

<400> SEQUENCE: 1
gttatttttt tcctcgatga agcc atg ggg agt gga ccc tct aat ttc gtc        51
                         Met Gly Ser Gly Pro Ser Asn Phe Val
                           1               5 aat cac gca cct gga gaa gca att gta acc ggt ttg gag aaa ggg gca        99
Asn His Ala Pro Gly Glu Ala Ile Val Thr Gly Leu Glu Lys Gly Ala
 10              15                  20                  25 gat aaa gta gct gga acg ata tca cat acg att tgg gaa gtg atc gcc       147
Asp Lys Val Ala Gly Thr Ile Ser His Thr Ile Trp Glu Val Ile Ala
                 30                  35                  40 gga tta gta gcc ttg ctg aca ttc tta gcg ttt ggc ttc tgg ttg ttc       195
Gly Leu Val Ala Leu Leu Thr Phe Leu Ala Phe Gly Phe Trp Leu Phe
             45                  50                  55 aag tat ctc caa aag aga aga gaa aga agg aga caa ctc act gag ttc       243
Lys Tyr Leu Gln Lys Arg Arg Glu Arg Arg Arg Gln Leu Thr Glu Phe
         60                  65                  70 caa aaa cgg tat cta cgg aat agc tac agg ttg agt gag atc cag aga       291
Gln Lys Arg Tyr Leu Arg Asn Ser Tyr Arg Leu Ser Glu Ile Gln Arg
     75                  80                  85 cct ata tca cag cac gaa tac gaa gac cca tac gag cca cca agt cgt       339
Pro Ile Ser Gln His Glu Tyr Glu Asp Pro Tyr Glu Pro Pro Ser Arg
 90                  95                 100                 105 agg aaa cca ccc cct cct cct tat agc aca tac gtc aac atc gat aat       387
Arg Lys Pro Pro Pro Pro Pro Tyr Ser Thr Tyr Val Asn Ile Asp Asn
                110                 115                 120 gtc tca gcc att tag tgatgagcaa cggagggcca ttattaagtt atgcttggca       442
Val Ser Ala Ile
            125 tttgctgacg gaggaacatc aggagccgat gtagatgagt tgatacgtcg catggcggca     502 ttagaggtat cgttagtaga gataaggcga gacctgacgg ttctagatgg ggatgtagcc     562 tctgtaatcc gtagactaca ggacgctgag gacgcgataa cggcattgtc caacgcgatg    622
```

-continued

```
caggtggtcc aatcacatat tgaagagata gttacgcaag ttcgaaaaca agtggagcag    682
atagcggctt tggagacggc ggtgactcag aacacgaagg acatagatag tgtgcgtagc    742
acggtaacgg atttaggatc cttagtgagt gcagagaaag tgaggttgga cggtgtggcg    802
agagatgtgt cgacacaggg actgtcaatc actgatttgc aggcgcgagt agctaaatta    862
gaaagggaag ctgaaccgac gtcgttcgaa tggccactga gaaaagatgc gaagagtgga    922
ttgctatcat tgaactggga tccttggttc ttagaaacga ctgaaatatt tggactctca    982
tgggcgcagt ctggagttga gatgggagcc acaactggac aaggagaatg gcatacacaa   1042
agtggtgatt acttgtacac cgtgagcctt aactttaaat tctacagata caggtctatg   1102
ggagcctttt cactctcaac cgggaatgcg ttgctgaacg gcccaaaggt ggagctacgt   1162
ataccatata ccacaggggg gactggccta gaaggatctg acctacaaaa catgacgcca   1222
tcgtccacca cgagatttcc gttgacgttc gtgacacgaa taacggtagg aggaagtgaa   1282
tataccatgc caattacggt gacaatacga cgaattagtg gtgtggatac aatcgtgcta   1342
actccagcgg atttgccagg cgccacaagc tatccatgtt atctgagggg ggagtcgata   1402
ttttactaca tgagggctag gcagatgacg tgattgcgtg aagagggact ctccccgtaa   1462
ggtgaagcac gatgggacgt gcgaggaaag ctattcatc                          1501
```

```
<210> SEQ ID NO 2
<211> LENGTH: 125
<212> TYPE: PRT
<213> ORGANISM: reptilian reovirus

<400> SEQUENCE: 2

Met Gly Ser Gly Pro Ser Asn Phe Val Asn His Ala Pro Gly Glu Ala
1               5                   10                  15

Ile Val Thr Gly Leu Glu Lys Gly Ala Asp Lys Val Ala Gly Thr Ile
            20                  25                  30

Ser His Thr Ile Trp Glu Val Ile Ala Gly Leu Val Ala Leu Leu Thr
        35                  40                  45

Phe Leu Ala Phe Gly Phe Trp Leu Phe Lys Tyr Leu Gln Lys Arg Arg
    50                  55                  60

Glu Arg Arg Arg Gln Leu Thr Glu Phe Gln Lys Arg Tyr Leu Arg Asn
65                  70                  75                  80

Ser Tyr Arg Leu Ser Glu Ile Gln Arg Pro Ile Ser Gln His Glu Tyr
                85                  90                  95

Glu Asp Pro Tyr Glu Pro Pro Ser Arg Arg Lys Pro Pro Pro Pro Pro
            100                 105                 110

Tyr Ser Thr Tyr Val Asn Ile Asp Asn Val Ser Ala Ile
        115                 120                 125
```

```
<210> SEQ ID NO 3
<211> LENGTH: 1501
<212> TYPE: DNA
<213> ORGANISM: reptilian reovirus
<220> FEATURE:
<221> NAME/KEY: CDS
<222> LOCATION: (386)..(1435)

<400> SEQUENCE: 3
gttatttttt tcctcgatga agccatgggg agtggaccct ctaatttcgt caatcacgca     60
cctggagaag caattgtaac cggtttggag aaaggggcag ataaagtagc tggaacgata    120
tcacatacga tttgggaagt gatcgccgga ttagtagcct tgctgacatt cttagcgttt    180
```

-continued

```
ggcttctggt tgttcaagta tctccaaaag agaagagaaa gaaggagaca actcactgag      240
ttccaaaaac ggtatctacg gaatagctac aggttgagtg agatccagag acctatatca      300
cagcacgaat acgaagaccc atacgagcca ccaagtcgta ggaaaccacc ccctcctcct      360
tatagcacat acgtcaacat cgata atg tct cag cca ttt agt gat gag caa        412
                             Met Ser Gln Pro Phe Ser Asp Glu Gln
                              1               5 cgg agg gcc att att aag tta tgc ttg gca ttt gct gac gga gga aca        460
Arg Arg Ala Ile Ile Lys Leu Cys Leu Ala Phe Ala Asp Gly Gly Thr
 10              15                  20                  25 tca gga gcc gat gta gat gag ttg ata cgt cgc atg gcg gca tta gag        508
Ser Gly Ala Asp Val Asp Glu Leu Ile Arg Arg Met Ala Ala Leu Glu
                 30                  35                  40 gta tcg tta gta gag ata agg cga gac ctg acg gtt cta gat ggg gat        556
Val Ser Leu Val Glu Ile Arg Arg Asp Leu Thr Val Leu Asp Gly Asp
                 45                  50                  55 gta gcc tct gta atc cgt aga cta cag gac gct gag gac gca ata acg        604
Val Ala Ser Val Ile Arg Arg Leu Gln Asp Ala Glu Asp Ala Ile Thr
             60                  65                  70 gca ttg tcc aac gcg atg cag gtg gtc caa tca cat att gaa gag ata        652
Ala Leu Ser Asn Ala Met Gln Val Val Gln Ser His Ile Glu Glu Ile
 75                  80                  85 gtt acg caa gtt cga aaa caa gtg gag cag ata gcg gct ttg gag acg        700
Val Thr Gln Val Arg Lys Gln Val Glu Gln Ile Ala Ala Leu Glu Thr
 90                  95                 100                 105 gcg gtg act cag aac acg aag gac ata gat agt gtg cgt agc acg gta        748
Ala Val Thr Gln Asn Thr Lys Asp Ile Asp Ser Val Arg Ser Thr Val
                110                 115                 120 acg gat tta gga tcc tta gtg agt gca gag aaa gtg agg ttg gac ggt        796
Thr Asp Leu Gly Ser Leu Val Ser Ala Glu Lys Val Arg Leu Asp Gly
                125                 130                 135 gtg gcg aga gat gtg tcg aca cag gga ctg tca atc act gat ttg cag        844
Val Ala Arg Asp Val Ser Thr Gln Gly Leu Ser Ile Thr Asp Leu Gln
                140                 145                 150 gcg cga gta gct aaa tta gaa agg gaa gct gaa ccg acg tcg ttc gaa        892
Ala Arg Val Ala Lys Leu Glu Arg Glu Ala Glu Pro Thr Ser Phe Glu
155                 160                 165 tgg cca ctg aga aaa gat gcg aag agt gga ttg cta tca ttg aac tgg        940
Trp Pro Leu Arg Lys Asp Ala Lys Ser Gly Leu Leu Ser Leu Asn Trp
170                 175                 180                 185 gat cct tgg ttc tta gaa acg act gaa ata ttt gga ctc tca tgg gcg        988
Asp Pro Trp Phe Leu Glu Thr Thr Glu Ile Phe Gly Leu Ser Trp Ala
                190                 195                 200 cag tct gga gtt gag atg gga gcc aca act gga caa gga gaa tgg cat       1036
Gln Ser Gly Val Glu Met Gly Ala Thr Thr Gly Gln Gly Glu Trp His
                205                 210                 215 aca caa agt ggt gat tac ttg tac acc gtg agc ctt aac ttt aaa ttc       1084
Thr Gln Ser Gly Asp Tyr Leu Tyr Thr Val Ser Leu Asn Phe Lys Phe
                220                 225                 230 tac aga tac agg tct atg gga gcc ttt tca ctc tca acc ggg aat gcg       1132
Tyr Arg Tyr Arg Ser Met Gly Ala Phe Ser Leu Ser Thr Gly Asn Ala
235                 240                 245 ttg ctg aac ggc cca aag gtg gag cta cgt ata cca tat acc aca ggg       1180
Leu Leu Asn Gly Pro Lys Val Glu Leu Arg Ile Pro Tyr Thr Thr Gly
250                 255                 260                 265 ggg act ggc cta gaa gga tct gac cta caa aac atg acg cca tcg tcc       1228
Gly Thr Gly Leu Glu Gly Ser Asp Leu Gln Asn Met Thr Pro Ser Ser
                270                 275                 280 acc acg aga ttt ccg ttg acg ttc gtg aca cga ata acg gta gga gga       1276
```

```
Thr Thr Arg Phe Pro Leu Thr Phe Val Thr Arg Ile Thr Val Gly Gly
            285                 290                 295 agt gaa tat acc atg cca att acg gtg aca ata cga cga att agt ggt     1324
Ser Glu Tyr Thr Met Pro Ile Thr Val Thr Ile Arg Arg Ile Ser Gly
            300                 305                 310 gtg gat aca atc gtg cta act cca gcg gat ttg cca ggc gcc aca agc     1372
Val Asp Thr Ile Val Leu Thr Pro Ala Asp Leu Pro Gly Ala Thr Ser
            315                 320                 325 tat cca tgt tat ctg agg ggg gag tcg ata ttt tac tac atg agg gct     1420
Tyr Pro Cys Tyr Leu Arg Gly Glu Ser Ile Phe Tyr Tyr Met Arg Ala
330                 335                 340                 345 agg cag atg acg tga ttgcgtgaag agggactctc cccgtaaggt gaagcacgat     1475
Arg Gln Met Thr gggacgtgcg aggaaagcta ttcatc                                        1501

<210> SEQ ID NO 4
<211> LENGTH: 349
<212> TYPE: PRT
<213> ORGANISM: reptilian reovirus

<400> SEQUENCE: 4

Met Ser Gln Pro Phe Ser Asp Glu Gln Arg Arg Ala Ile Ile Lys Leu
1               5                   10                  15

Cys Leu Ala Phe Ala Asp Gly Gly Thr Ser Gly Ala Asp Val Asp Glu
            20                  25                  30

Leu Ile Arg Arg Met Ala Ala Leu Glu Val Ser Leu Val Glu Ile Arg
        35                  40                  45

Arg Asp Leu Thr Val Leu Asp Gly Asp Val Ala Ser Val Ile Arg Arg
    50                  55                  60

Leu Gln Asp Ala Glu Asp Ala Ile Thr Ala Leu Ser Asn Ala Met Gln
65                  70                  75                  80

Val Val Gln Ser His Ile Glu Glu Ile Val Thr Gln Val Arg Lys Gln
                85                  90                  95

Val Glu Gln Ile Ala Ala Leu Glu Thr Ala Val Thr Gln Asn Thr Lys
            100                 105                 110

Asp Ile Asp Ser Val Arg Ser Thr Val Thr Asp Leu Gly Ser Leu Val
        115                 120                 125

Ser Ala Glu Lys Val Arg Leu Asp Gly Val Ala Arg Asp Val Ser Thr
    130                 135                 140

Gln Gly Leu Ser Ile Thr Asp Leu Gln Ala Arg Val Ala Lys Leu Glu
145                 150                 155                 160

Arg Glu Ala Glu Pro Thr Ser Phe Glu Trp Pro Leu Arg Lys Asp Ala
                165                 170                 175

Lys Ser Gly Leu Leu Ser Leu Asn Trp Asp Pro Trp Phe Leu Glu Thr
            180                 185                 190

Thr Glu Ile Phe Gly Leu Ser Trp Ala Gln Ser Gly Val Glu Met Gly
        195                 200                 205

Ala Thr Thr Gly Gln Gly Glu Trp His Thr Gln Ser Gly Asp Tyr Leu
    210                 215                 220

Tyr Thr Val Ser Leu Asn Phe Lys Phe Tyr Arg Tyr Arg Ser Met Gly
225                 230                 235                 240

Ala Phe Ser Leu Ser Thr Gly Asn Ala Leu Leu Asn Gly Pro Lys Val
                245                 250                 255

Glu Leu Arg Ile Pro Tyr Thr Thr Gly Gly Thr Gly Leu Glu Gly Ser
            260                 265                 270
```

```
            Asp Leu Gln Asn Met Thr Pro Ser Ser Thr Thr Arg Phe Pro Leu Thr
                    275                 280                 285

Phe Val Thr Arg Ile Thr Val Gly Gly Ser Glu Tyr Thr Met Pro Ile
                290                 295                 300

Thr Val Thr Ile Arg Arg Ile Ser Gly Val Asp Thr Ile Val Leu Thr
            305                 310                 315                 320

Pro Ala Asp Leu Pro Gly Ala Thr Ser Tyr Pro Cys Tyr Leu Arg Gly
                            325                 330                 335

Glu Ser Ile Phe Tyr Tyr Met Arg Ala Arg Gln Met Thr
                        340                 345

<210> SEQ ID NO 5
<211> LENGTH: 1398
<212> TYPE: DNA
<213> ORGANISM: aquareovirus
<220> FEATURE:
<221> NAME/KEY: CDS
<222> LOCATION: (8)..(484)
<220> FEATURE:
<221> NAME/KEY: misc_feature
<222> LOCATION: (8)..(58)
<223> OTHER INFORMATION: Initiator codon unknown; coding sequence begins
      at a position within the first 17 codon

<400> SEQUENCE: 5 gttttag tca atc atc ctg ggg aat acc atc tca aac acc gtt cag tac         49
        Ser Ile Ile Leu Gly Asn Thr Ile Ser Asn Thr Val Gln Tyr
          1               5                  10 acg gta ctg cag atc gac aga tct tgc tgt atc aaa acc agc ctc acc         97
Thr Val Leu Gln Ile Asp Arg Ser Cys Cys Ile Lys Thr Ser Leu Thr
 15                  20                  25                  30 gcc act tcc gaa gcc act tcc tgg gcc atc ccc cct ctc gca atc tgt        145
Ala Thr Ser Glu Ala Thr Ser Trp Ala Ile Pro Pro Leu Ala Ile Cys
                 35                  40                  45 tgc tgc tgt tgc atc tgc tgt acc ggc gga cta tat ctc gtt cat tct        193
Cys Cys Cys Cys Ile Cys Cys Thr Gly Gly Leu Tyr Leu Val His Ser
             50                  55                  60 gga cgt ttt cca ggc ctc agc cga agg ttg gac gtg ctc gga ggt tcg        241
Gly Arg Phe Pro Gly Leu Ser Arg Arg Leu Asp Val Leu Gly Gly Ser
         65                  70                  75 ggg tca acc cca aaa cac tcg ctg cgt agc cac ggc acc caa agc cac        289
Gly Ser Thr Pro Lys His Ser Leu Arg Ser His Gly Thr Gln Ser His
     80                  85                  90 gtg tac atc gcg tta gct tca gtg att cta gtg act cta gtg ata tct        337
Val Tyr Ile Ala Leu Ala Ser Val Ile Leu Val Thr Leu Val Ile Ser
 95                 100                 105                 110 ctg atc tgg aat tgc ctc ggc acg ggt ctc atc ctc tgg cgc att cat        385
Leu Ile Trp Asn Cys Leu Gly Thr Gly Leu Ile Leu Trp Arg Ile His
                115                 120                 125 tca ggc ctg aag tcg atc gcc acc gcc ctc gtc cct caa cgc aag tcc        433
Ser Gly Leu Lys Ser Ile Ala Thr Ala Leu Val Pro Gln Arg Lys Ser
            130                 135                 140 agc aga cat ctt tca tcc cgc tcg tac cac tca gct ccg gat caa gtt        481
Ser Arg His Leu Ser Ser Arg Ser Tyr His Ser Ala Pro Asp Gln Val
        145                 150                 155 tag acgatgggat cgtacgctct caaccctcac gggattcgcg gccccacgag             534
caatttgagg attggcttca acaagcacat ctcctacgac caggacgagt ttccggatct      594 accaaccccct tcacctgacc acattcccga ctgggtgacg gatcatgaca agttcaacgg     654
tcatcccctc cccctcgtct acgatggacg tctgacaccc atcacgggtc ctcaccatct     714
```

```
ttgggagcct gacagttatg tagagtggca gacctggggg tgcctccgac ccttctctcc      774
tttcagcgtt tggccaccaa cggtaccgaa ctggttcagc cgtaaggtcc tccacgtctt      834
cagcaacatg tccccgtacg cctgcgctgc tgagaagagt cccaatcccc ttccctactg      894
gcgtttgaat gatcagggtc gtgactggag cgtattctgg gacttaattt ggcgatgtgc      954
tcagacacgt ggtgctcgca tctgttttgc gaagaccccc ttcatccaga cgatgctacg     1014
cctgactgac gatcagctgt cccgtcttcc atccgctgag gatccaatca gtctcttaaa     1074
catcgcagga tgggacgccc ttcttctcaa cggtcttccc cctaacctgg tgcgagcatt     1134
gatgaggtcc cctccaaacc cagaggtcgt tgagctggat ctgctcgtct cctggttcga     1194
tgtcgtgatt cgtattccct atgacgtgca acacccccta ggccttggtt tcagccctga     1254
tcaattttgg actcatccgt tcgtcgtcct gtgctacctg cgctggcgtt tgttgggagg     1314
tgacgactag gatggcgtcc gcgacagttg aggcctgggc ctcggggatt tagtcccctg     1374
tcgccagcgt gactgctatt catc                                            1398
```

<210> SEQ ID NO 6
<211> LENGTH: 158
<212> TYPE: PRT
<213> ORGANISM: aquareovirus
<220> FEATURE:
<221> NAME/KEY: misc_feature
<222> LOCATION: (8)..(58)
<223> OTHER INFORMATION: Initiator codon unknown; coding sequence begins
      at a position within the first 17 codon

<400> SEQUENCE: 6

```
Ser Ile Ile Leu Gly Asn Thr Ile Ser Asn Thr Val Gln Tyr Thr Val
1               5                   10                  15

Leu Gln Ile Asp Arg Ser Cys Cys Ile Lys Thr Ser Leu Thr Ala Thr
            20                  25                  30

Ser Glu Ala Thr Ser Trp Ala Ile Pro Pro Leu Ala Ile Cys Cys Cys
        35                  40                  45

Cys Cys Ile Cys Cys Thr Gly Gly Leu Tyr Leu Val His Ser Gly Arg
    50                  55                  60

Phe Pro Gly Leu Ser Arg Arg Leu Asp Val Leu Gly Gly Ser Gly Ser
65                  70                  75                  80

Thr Pro Lys His Ser Leu Arg Ser His Gly Thr Gln Ser His Val Tyr
                85                  90                  95

Ile Ala Leu Ala Ser Val Ile Leu Val Thr Leu Val Ile Ser Leu Ile
            100                 105                 110

Trp Asn Cys Leu Gly Thr Gly Leu Ile Leu Trp Arg Ile His Ser Gly
        115                 120                 125

Leu Lys Ser Ile Ala Thr Ala Leu Val Pro Gln Arg Lys Ser Ser Arg
    130                 135                 140

His Leu Ser Ser Arg Ser Tyr His Ser Ala Pro Asp Gln Val
145                 150                 155
```

<210> SEQ ID NO 7
<211> LENGTH: 1398
<212> TYPE: DNA
<213> ORGANISM: aquareovirus
<220> FEATURE:
<221> NAME/KEY: CDS
<222> LOCATION: (488)..(1324)

<400> SEQUENCE: 7

```
gttttagtca atcatcctgg ggaataccat ctcaaacacc gttcagtaca cggtactgca       60
```

-continued

```
gatcgacaga tcttgctgta tcaaaaccag cctcaccgcc acttccgaag ccacttcctg      120
ggccatcccc cctctcgcaa tctgttgctg ctgttgcatc tgctgtaccg gcggactata      180
tctcgttcat tctggacgtt ttccaggcct cagccgaagg ttggacgtgc tcggaggttc      240
ggggtcaacc ccaaaacact cgctgcgtag ccacggcacc caaagccacg tgtacatcgc      300
gttagcttca gtgattctag tgactctagt gatatctctg atctggaatt gcctcggcac      360
gggtctcatc ctctggcgca ttcattcagg cctgaagtcg atcgccaccg ccctcgtccc      420
tcaacgcaag tccagcagac atctttcatc ccgctcgtac cactcagctc cggatcaagt      480
```

| | | | | | | | | | | | | | | | | | |
|---|---|---|---|---|---|---|---|---|---|---|---|---|---|---|---|---|---|
| ttagacg atg | gga | tcg | tac | gct | ctc | aac | cct | cac | ggg | att | cgc | ggc | ccc | | | | 529 |
| | Met | Gly | Ser | Tyr | Ala | Leu | Asn | Pro | His | Gly | Ile | Arg | Gly | Pro | | | |
| | 1 | | | 5 | | | | | 10 | | | | | | | | |
| acg | agc | aat | ttg | agg | att | ggc | ttc | aac | aag | cac | atc | tcc | tac | gac | cag | | 577 |
| Thr | Ser | Asn | Leu | Arg | Ile | Gly | Phe | Asn | Lys | His | Ile | Ser | Tyr | Asp | Gln | | |
| 15 | | | | 20 | | | | | 25 | | | | | 30 | | | |
| gac | gag | ttt | ccg | gat | cta | cca | acc | cct | tca | cct | gac | cac | att | ccc | gac | | 625 |
| Asp | Glu | Phe | Pro | Asp | Leu | Pro | Thr | Pro | Ser | Pro | Asp | His | Ile | Pro | Asp | | |
| | | | | 35 | | | | 40 | | | | | 45 | | | | |
| tgg | gtg | acg | gat | cat | gac | aag | ttc | aac | ggt | cat | ccc | ctc | ccc | ctc | gtc | | 673 |
| Trp | Val | Thr | Asp | His | Asp | Lys | Phe | Asn | Gly | His | Pro | Leu | Pro | Leu | Val | | |
| | 50 | | | | | 55 | | | | | 60 | | | | | | |
| tac | gat | gga | cgt | ctg | aca | ccc | atc | acg | ggt | cct | cac | cat | ctt | tgg | gag | | 721 |
| Tyr | Asp | Gly | Arg | Leu | Thr | Pro | Ile | Thr | Gly | Pro | His | His | Leu | Trp | Glu | | |
| 65 | | | | | 70 | | | | | 75 | | | | | | | |
| cct | gac | agt | tat | gta | gag | tgg | cag | acc | tgg | ggg | tgc | ctc | cga | ccc | ttc | | 769 |
| Pro | Asp | Ser | Tyr | Val | Glu | Trp | Gln | Thr | Trp | Gly | Cys | Leu | Arg | Pro | Phe | | |
| 80 | | | | | 85 | | | | | 90 | | | | | | | |
| tct | cct | ttc | agc | gtt | tgg | cca | cca | acg | gta | ccg | aac | tgg | ttc | agc | cgt | | 817 |
| Ser | Pro | Phe | Ser | Val | Trp | Pro | Pro | Thr | Val | Pro | Asn | Trp | Phe | Ser | Arg | | |
| 95 | | | | 100 | | | | | 105 | | | | | 110 | | | |
| aag | gtc | ctc | cac | gtc | ttc | agc | aac | atg | tcc | ccg | tac | gcc | tgc | gct | gct | | 865 |
| Lys | Val | Leu | His | Val | Phe | Ser | Asn | Met | Ser | Pro | Tyr | Ala | Cys | Ala | Ala | | |
| | | | | 115 | | | | | 120 | | | | | 125 | | | |
| gag | aag | agt | ccc | aat | ccc | ctt | ccc | tac | tgg | cgt | ttg | aat | gat | cag | ggt | | 913 |
| Glu | Lys | Ser | Pro | Asn | Pro | Leu | Pro | Tyr | Trp | Arg | Leu | Asn | Asp | Gln | Gly | | |
| | | 130 | | | | | 135 | | | | | 140 | | | | | |
| cgt | gac | tgg | agc | gta | ttc | tgg | gac | tta | att | tgg | cga | tgt | gct | cag | aca | | 961 |
| Arg | Asp | Trp | Ser | Val | Phe | Trp | Asp | Leu | Ile | Trp | Arg | Cys | Ala | Gln | Thr | | |
| | 145 | | | | | 150 | | | | | 155 | | | | | | |
| cgt | ggt | gct | cgc | atc | tgt | ttt | gcg | aag | acc | ccc | ttc | atc | cag | acg | atg | | 1009 |
| Arg | Gly | Ala | Arg | Ile | Cys | Phe | Ala | Lys | Thr | Pro | Phe | Ile | Gln | Thr | Met | | |
| | 160 | | | | 165 | | | | | 170 | | | | | | | |
| cta | cgc | ctg | act | gac | gat | cag | ctg | tcc | cgt | ctt | cca | tcc | gct | gag | gat | | 1057 |
| Leu | Arg | Leu | Thr | Asp | Asp | Gln | Leu | Ser | Arg | Leu | Pro | Ser | Ala | Glu | Asp | | |
| 175 | | | | 180 | | | | | 185 | | | | | 190 | | | |
| cca | atc | agt | ctc | tta | aac | atc | gca | gga | tgg | gac | gcc | ctt | ctt | ctc | aac | | 1105 |
| Pro | Ile | Ser | Leu | Leu | Asn | Ile | Ala | Gly | Trp | Asp | Ala | Leu | Leu | Leu | Asn | | |
| | | | | 195 | | | | | 200 | | | | | 205 | | | |
| ggt | ctt | ccc | cct | aac | ctg | gtg | cga | gca | ttg | atg | agg | tcc | cct | cca | aac | | 1153 |
| Gly | Leu | Pro | Pro | Asn | Leu | Val | Arg | Ala | Leu | Met | Arg | Ser | Pro | Pro | Asn | | |
| | | | 210 | | | | | 215 | | | | | 220 | | | | |
| cca | gag | gtc | gtt | gag | ctg | gat | ctg | ctc | gtc | tcc | tgg | ttc | gat | gtc | gtg | | 1201 |
| Pro | Glu | Val | Val | Glu | Leu | Asp | Leu | Leu | Val | Ser | Trp | Phe | Asp | Val | Val | | |
| | | 225 | | | | | 230 | | | | | 235 | | | | | |
| att | cgt | att | ccc | tat | gac | gtg | caa | cac | ccc | cta | ggc | ctt | ggt | ttc | agc | | 1249 |
| Ile | Arg | Ile | Pro | Tyr | Asp | Val | Gln | His | Pro | Leu | Gly | Leu | Gly | Phe | Ser | | |
| | 240 | | | | 245 | | | | | 250 | | | | | | | |

```
cct gat caa ttt tgg act cat ccg ttc gtc gtc ctg tgc tac ctg cgc      1297
Pro Asp Gln Phe Trp Thr His Pro Phe Val Val Leu Cys Tyr Leu Arg
255                 260                 265                 270 tgg cgt ttg ttg gga ggt gac gac tag gatggcgtcc gcgacagttg            1344
Trp Arg Leu Leu Gly Gly Asp Asp
                275 aggcctgggc ctcggggatt tagtcccctg tcgccagcgt gactgctatt catc          1398
```

<210> SEQ ID NO 8
<211> LENGTH: 278
<212> TYPE: PRT
<213> ORGANISM: aquareovirus

<400> SEQUENCE: 8

```
Met Gly Ser Tyr Ala Leu Asn Pro His Gly Ile Arg Gly Pro Thr Ser
1               5                   10                  15

Asn Leu Arg Ile Gly Phe Asn Lys His Ile Ser Tyr Asp Gln Asp Glu
            20                  25                  30

Phe Pro Asp Leu Pro Thr Pro Ser Pro Asp His Ile Pro Asp Trp Val
        35                  40                  45

Thr Asp His Asp Lys Phe Asn Gly His Pro Leu Pro Leu Val Tyr Asp
50                  55                  60

Gly Arg Leu Thr Pro Ile Thr Gly Pro His His Leu Trp Glu Pro Asp
65                  70                  75                  80

Ser Tyr Val Glu Trp Gln Thr Trp Gly Cys Leu Arg Pro Phe Ser Pro
                85                  90                  95

Phe Ser Val Trp Pro Pro Thr Val Pro Asn Trp Phe Ser Arg Lys Val
            100                 105                 110

Leu His Val Phe Ser Asn Met Ser Pro Tyr Ala Cys Ala Ala Glu Lys
        115                 120                 125

Ser Pro Asn Pro Leu Pro Tyr Trp Arg Leu Asn Asp Gln Gly Arg Asp
130                 135                 140

Trp Ser Val Phe Trp Asp Leu Ile Trp Arg Cys Ala Gln Thr Arg Gly
145                 150                 155                 160

Ala Arg Ile Cys Phe Ala Lys Thr Pro Phe Ile Gln Thr Met Leu Arg
                165                 170                 175

Leu Thr Asp Asp Gln Leu Ser Arg Leu Pro Ser Ala Glu Asp Pro Ile
            180                 185                 190

Ser Leu Leu Asn Ile Ala Gly Trp Asp Ala Leu Leu Leu Asn Gly Leu
        195                 200                 205

Pro Pro Asn Leu Val Arg Ala Leu Met Arg Ser Pro Asn Pro Glu
210                 215                 220

Val Val Glu Leu Asp Leu Leu Ser Trp Phe Asp Val Val Ile Arg
225                 230                 235                 240

Ile Pro Tyr Asp Val Gln His Pro Leu Gly Leu Gly Phe Ser Pro Asp
                245                 250                 255

Gln Phe Trp Thr His Pro Phe Val Val Leu Cys Tyr Leu Arg Trp Arg
            260                 265                 270

Leu Leu Gly Gly Asp Asp
        275
```

<210> SEQ ID NO 9
<211> LENGTH: 8
<212> TYPE: PRT
<213> ORGANISM: reptilian reovirus
<220> FEATURE:
<221> NAME/KEY: VARIANT -continued

```
<222> LOCATION: (2)..(5)
<223> OTHER INFORMATION: small uncharged residues
<220> FEATURE:
<221> NAME/KEY: VARIANT
<222> LOCATION: (6)..(6)
<223> OTHER INFORMATION: small uncharged residue; not proline
<220> FEATURE:
<221> NAME/KEY: misc_feature
<222> LOCATION: (7)..(8)
<223> OTHER INFORMATION: Xaa can be any naturally occurring amino acid

<400> SEQUENCE: 9

Gly Xaa Xaa Xaa Xaa Xaa Xaa Xaa
1               5
```

MEMBRANE FUSION PROTEINS DERIVED FROM REOVIRUS

CROSS REFERENCE TO RELATED APPLICATION

This application is a continuation application of application Ser. No. 10/433,276, filed Jun. 2, 2003 now abandoned, the content of which is herein incorporated by reference.

FIELD OF THE INVENTION

The present invention relates to a novel class of proteins that promote membrane fusion. The proteins and the polynucleotides encoding them are derived from the family Reoviridae.

BACKGROUND OF THE INVENTION

Membrane fusion reactions are common in eukaryotic cells. Membranes are fused intracellularly in processes including endocytosis, organelle formation, inter-organelle traffic, and constitutive and regulated exocytosis. Intercellularly, membrane fusion occurs during sperm-egg fusion and myoblast fusion.

Membrane fusion has been induced artificially by the use of liposomes, in which the cell membrane is fused with the liposomal membrane, and by various chemicals or lipids, which induce cell-cell fusion to produce heterokaryons. Naturally occurring proteins shown to induce fusion of biological membranes are mainly fusion proteins of enveloped viruses.

In liposome-based delivery systems, liposomes are used to encapsulate bioactive molecules inside lipid vesicles for delivery into the cell. However, the polar lipid head groups oriented on both surfaces of the lipid bilayer, along with an associated water layer, make spontaneous membrane fusion thermodynamically unfavorable.

Various chemicals or lipids have been used to promote membrane fusion. However, these reagents usually exhibit cytotoxic effects (see, for example, Iwamoto et al., in Biol. Pharm. Bull. 19:860-863 (1996) and Mizuguchi et al., in Biochem. Biophys. Res. Commun., 218:402-407 (1996)).

It is generally believed that membrane fusion under physiological conditions is protein-mediated. This has led to the development of liposomes that contain fusion-promoting proteins (proteoliposomes), with decreased cytotoxicity (see, for example, Cheng, Hum. Gene Ther. 7:275-282 (1996); Hara et al., Gene 159:167-174 (1995); and Findeis et al., Trends Biotechnol., 11:202-205 (1993)).

The only proteins conclusively shown to induce intercellular fusion of biological membranes are those of enveloped viruses and two proteins from nonenveloped viruses. All enveloped viruses encode proteins responsible for fusion of the viral envelope with the cell membrane. These viral fusion proteins are essential for infection of susceptible cells. The mechanism of action of fusion proteins from enveloped viruses have served as a paradigm for protein-mediated membrane fusion (see, for example, White, Ann. Rev. Physiol., 52:675-697 (1990); and White, Science, 258:917-924 (1992)).

Most enveloped virus fusion proteins are relatively large, multimeric, type I membrane proteins, as typified by the influenza virus HA protein, a low pH-activated fusion protein, and the Sendai virus F protein, which functions at neutral pH. These are structural proteins of the virus with the majority of the fusion protein oriented on the external surface of the virion to facilitate interactions between the virus particle and the cell membrane.

According to the mechanism of action of fusion proteins from enveloped viruses, fusion of the viral envelope with the cell membrane is mediated by an amphipathic alpha-helical region, referred to as a fusion peptide motif, that is present in the viral fusion protein. This type of fusion peptide motif is typically 17 to 28 residues long, hydrophobic (average hydrophobicity of about $0.6\pm0.1$), and contains a high content of glycine and alanine, typically $36\%\pm7\%$ (White, Annu. Rev. Physiol., 52:675-697 (1990).

All of the enveloped virus fusion proteins are believed to function via extensive conformational changes that, by supplying the energy to overcome the thermodynamic barrier, promote membrane fusion. These conformational changes are frequently mediated by heptad repeat regions that form coiled coil structures (see Skehel and Wiley, Cell, 95:871-874 (1998)). Recognition of the importance of fusion peptide motifs in triggering membrane fusion has resulted in the use of small peptides containing fusion peptide motifs to enhance liposome-cell fusion (see, for example, Muga et al., Biochemistry 33:4444-4448 (1994)).

Enveloped virus fusion proteins also trigger cell-cell fusion, resulting in the formation of polykaryons (syncytia). Synthesis of the viral fusion protein inside the infected cell results in transport of the fusion protein through the endoplasmic reticulum and Golgi transport system to the cell membrane, an essential step in the assembly and budding of infectious progeny virus particles from the infected cell (Petterson, Curr. Top. Micro. Immunol., 170:67-106 (1991)). The synthesis, transport, and folding of the fusion protein is facilitated by a variety of components, including signal peptides to target the protein to the intracellular transport pathway, glycosylation signals for N-linked carbohydrate addition to the protein, and a transmembrane domain to anchor the protein in the cell membrane. These proteins have been used in reconstituted proteoliposomes ('virosomes') for enhanced, protein-mediated liposome-cell fusion in both cell culture and in vivo (see, for example, Ramani et al., FEBS Lett., 404:164-168 (1997); Scheule et al., Am. J. Respir. Cell Mol. Biol., 13:330-343 (1995); and Grimaldi, Res. Virol., 146:289-293 (1995)).

Unlike enveloped viruses, nonenveloped viruses generally do not encode fusion proteins since the absence of a viral membrane precludes membrane fusion-mediated entry. Because progeny virus particles of nonenveloped viruses do not need to acquire a lipid envelope, these viruses usually do not bud from infected cells but, rather, are released by cell lysis. As a result, nonenveloped viruses do not express fusion proteins on the surface of infected cells and, hence, generally do not induce syncytium formation.

Selected members of the family Reoviridae, however, do induce syncytium formation (see Duncan et al., Virology, 212:752-756 (1995), Duncan, Virology, 260:316-328 (1999), and references therein). Reoviridae are a family of nonenveloped viruses containing segmented double-stranded RNA (dsRNA) genomes (see, for example, Nibert et al., Reoviruses and their replication, In: Fundamental Virology, 3rd Edition, B. N. Fields, D. M. Knipe and P. M. Howley (Eds), Lippincott-Raven Press, NY (1996)).

Of the family Reoviridae, the genus *Orthoreovirus* contains two distinct subgroups typified by the prototypical avian and the mammalian reoviruses (see Duncan, Virology, 260: 316-328 (1999)). The avian reoviruses (ARV) are all fusogenic and induce rapid and extensive cell-cell fusion, resulting in syncytium formation in infected cell cultures (see Robertson and Wilcox, Vet. Bull., 56:726-733 (1986)).

Mammalian reoviruses generally are not fusogenic. However, there are at least two exceptions. One was isolated from a flying fox and is named Nelson Bay virus (NBV) (see Gard and Compans, J. Virol., 6:100-106 (1970)). The other was isolated from a baboon and is referred to as Baboon Reovirus (BRV) (see Duncan et al., Virology, 212:752-756 (1995)).

Fusogenic reoviruses have also been isolated from poikilothermic hosts. Two strains of reptilian reoviruses (RRV, a member of the *Orthoreovirus* genus) that induce syncytium formation have been isolated from snakes (see Ahne et al., Arch. Virol. 94:135-139 (1987), and Vieler et al., Arch. Virol. 138:341-344 (1994)). In addition, members of the genus *Aquareovirus* (AQV) that infect exclusively piscine (fish) host species, also induce cell-cell fusion (see Samal et al., J. Virol. 64:5235-5240 (1990)). These viruses together represent the few known examples of nonenveloped viruses capable of inducing membrane fusion.

To date, two membrane fusion proteins have been identified and sequenced from nonenveloped viruses: the p10 protein from two strains of ARV and from NBV, and the p15 protein from BRV. The p10 proteins share 33% amino acid identity between ARV and NBV and are clearly homologous proteins. The p15 protein from BRV is not homologous to p10 and appears to belong to a different class. The amino acid sequences of both the p10 and p15 proteins contain fusion peptide motifs (residues 9-24 of ARV and NBV and residues 68-87 of BRV, WO99/24582, published May 20, 1999; the p10 protein is referred to as "p11" in WO99/24582). The fusion peptide motif from the p10 protein (Shmulevitz and Duncan, EMBO J., 19:902-912 (2000)), however, is atypical in that it is much less hydrophobic than is observed in typical fusion motifs from enveloped viruses. The hydrophobicity of the fusion motif from p10 is estimated to be about 0.3 to 0.4, in contrast to the typical values of 0.6±0.1. Nevertheless, the fusion motif from p10 still contains the heptad repeats seen in more typical fusion motifs; i.e. seven-residue sequences in which residues at positions 1 and 4 are apolar; (See FIG. 6 which shows the heptad configuration of p10). It is generally thought that the conserved apolar residues serve to form the hydrophobic face of amphipathic helices which are important for membrane-interactive properties. The presence of heptad repeats in p10 and p15 suggests that these proteins promote membrane fusion by a mechanism similar to that of membrane fusion proteins from enveloped viruses.

SUMMARY OF THE INVENTION

According to the present invention, a new class of membrane fusion proteins is described which is derived from Reoviridae and whose amino acid sequence is free of fusion peptide motifs.

In one aspect, members of this class are membrane fusion proteins which are encoded by the genome of the family Reoviridae, which comprise at least one transmembrane domain, and whose amino acid sequence is free of any fusion peptide motifs. A fusion peptide motif (type I) is an amino acid sequence typically 17 to 28 residues long, with a hydrophobicity of about 0.6 to 0.7, and whose content of alanine plus glycine is about 29 to 43%. A fusion peptide motif (type II) is 16 to 20 residues long, has a hydrophobicity value about 0.3 to 0.4, has an alanine plus glycine content of about 29 to 43%; and contains a heptad repeat.

In another aspect, the proteins of the invention are membrane fusion proteins whose amino acid sequences are free of any fusion peptide motifs, as defined above, and which are related to Reoviridae in that they comprise an amino acid sequence which has at least 33% overall identity to the membrane fusion protein encoded by Reoviridae, and comprise a transmembrane domain whose amino acid sequence has at least 60% amino acid sequence identity to the transmembrane domain of the membrane fusion protein encoded by Reoviridae.

In one embodiment, the proteins of the invention are encoded by, or related to, the genome of *Orthoreovirus* or *Aquareovirus*, or the genome of a reovirus which naturally infects a poikilothermic host. Specifically, in one embodiment, the proteins of the invention are proteins comprising an amino acid sequence of SEQ ID NO:2 or SEQ ID NO:6. In another embodiment, the proteins of the invention are membrane fusion proteins whose amino acid sequences are free of any fusion peptide motif, as defined above, and which are related to *Orthoreovirus* or *Aquareovirus* in that they comprise an amino acid sequence which has at least 33% overall identity to the membrane fusion protein encoded by *Orthoreovirus* or *Aquareovirus*, and comprise a transmembrane domain whose amino acid sequence has at least 60% amino acid sequence identity to the transmembrane domain of the membrane fusion protein encoded by *Orthoreovirus* or *Aquareovirus*.

In another embodiment, the proteins of the invention are membrane fusion proteins whose amino acid sequence is free of a fusion peptide motif as defined above, which comprise an amino acid sequence which has at least 33% identity overall to SEQ ID NO:2, and which comprises a transmembrane domain whose amino acid sequence has at least 60% amino acid sequence identity to the sequence from residue 39 to 57 of SEQ ID NO:2.

In another embodiment, the proteins of the invention are membrane fusion proteins whose amino acid sequence is free of a fusion peptide motif as defined above, which comprise an amino acid sequence which has at least 33% identity overall to SEQ ID NO:6, and which comprises a transmembrane domain whose amino acid sequence has at least 60% amino acid sequence identity to the predicted first transmembrane sequence 5' WAIPPLAICCCCICCTGGLYLV 3' of SEQ ID NO:6, or has at least 60% amino acid sequence identity to the predicted second transmembrane sequence 5' YIALASVIL-VTLVISLIWNCLGTGLIL 3' of SEQ ID NO: 6.

In another embodiment, the amino acid sequences encoded by, or related to, the genome of Reoviridae, comprise neutral or basic proteins, i.e. they have an isoelectric point equal to or greater than 7.

In another embodiment, the proteins of the invention further comprises a positive cluster which consists of at least three positively charged amino acid residues within a contiguous sequence of at most 25 residues, wherein the contiguous sequence is within at most 100 residues flanking the transmembrane domain at the C-terminal side.

In another embodiment, the proteins of the invention, particularly those related to p14, further comprise a non-transmembrane domain which comprises a polyproline motif comprising at least 3 contiguous proline residues.

In another embodiment, the proteins of the invention further comprise a fatty acylation sequence such as a myristylation consensus sequence.

Another aspect of the invention provides an isolated polynucleotide encoding the proteins of the invention, specifically an isolated polynucleotide comprising SEQ ID NO:1 or SEQ ID NO:5, or degenerate variations thereof which encode the same amino acid sequences, or splice variant nucleotide sequences thereof. The isolated polynucleotide of the invention are expressed by being operatively associated with a promoter, which may be an inducible promoter.

Another aspect of the invention provides a cell which contains the proteins or polynucleotides of the invention.

Another aspect of the invention provides a liposome which contains the proteins or polynucleotides of the invention. In an embodiment where liposomes are used to deliver a bioactive drug to a cell, the liposomes or proteoliposomes contain both the protein of the invention and the bioactive drug.

Another aspect of the invention provides an antibody reactive against the protein of the invention.

Another aspect of the invention provides a method to promote fusion between two or more membranes, comprising contacting the membranes to be fused with an effective amount of the protein of the invention. In one embodiment, the membranes are cell membranes, liposome membranes or proteoliposome membranes, depending on whether cell-cell, liposome-liposome, or cell-liposome fusion is required.

In one embodiment, fusion between cells is effected by expressing the membrane fusion proteins of the invention in the cell(s) which are to undergo fusion.

In another embodiment, the fusion method of the invention is used to produce heterokaryons, particularly hybridoma cells for the production of monoclonal antibodies, cytokines, or immune modulators. Where the hybridoma cells produce monoclonal antibodies, the membranes are from an immortalized cell and an antibody-synthesizing cell.

BRIEF DESCRIPTION OF THE FIGURES

FIG. 1 consists of schematic diagrams of reovirus fusion protein-encoding genome segments.

FIG. 2 presents the nucleotide sequence of the bicistronic RRV S1 genome segment (SEQ ID NO:1), and the predicted amino acid sequences of the first open reading frame (ORF) encoding the p14 fusion protein (SEQ ID NO:2) and the second ORF encoding the unrelated sigma C cell attachment protein (SEQ ID NO:4).

FIG. 3 presents the nucleotide sequence of the polycistronic AQV genome segment 7 (SEQ ID NO:5), and the predicted amino acid sequences of the 5'-proximal ORF encoding the p16 fusion protein (SEQ ID NO:6) and the 3'-proximal ORF encoding the unrelated nonstructural virus protein NS28 (SEQ ID NO:8).

FIG. 4 presents the amino acid sequence of the RRV p14 fusion protein (SEQ ID NO:2). The predicted transmembrane domain is overlined and labeled. The cluster of positively charged amino acids is labeled with a + symbol. The polyproline region near the C-terminus is overlined and labeled (pro). The N-terminal consensus myristylation sequence (MGXXXS/T) is indicated (myr).

FIG. 5 presents the amino acid sequence of the AQV p16 fusion protein (SEQ ID NO:6). The predicted transmembrane domains are overlined and labeled. The clusters of positively charged amino acids adjacent to the transmembrane domains are labeled with a + symbol.

FIG. 6 is a schematic depiction of the apolar amino acids within the fusion peptide motifs of the p10 proteins from ARV and NBV. The heptad repeats are thought to constitute the hydrophobic faces of amphipathic helices, which are thought to be important for interaction of this type of membrane fusion protein with the membrane.

DETAILED DESCRIPTION

Figure 1A:
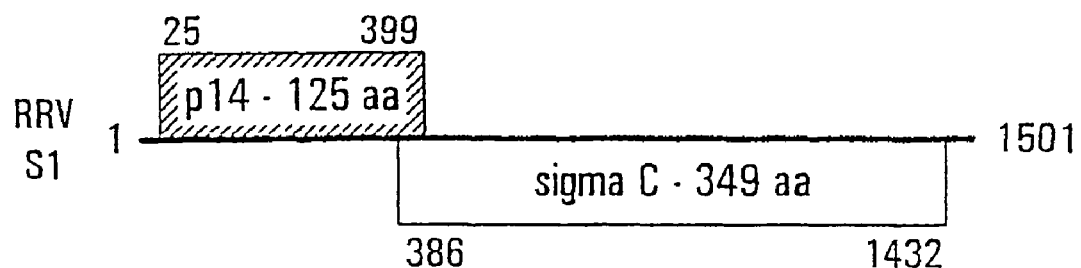
FIG. 1A presents the S1 genome segment from reptilian reovirus (RRV).
Figure 1B:
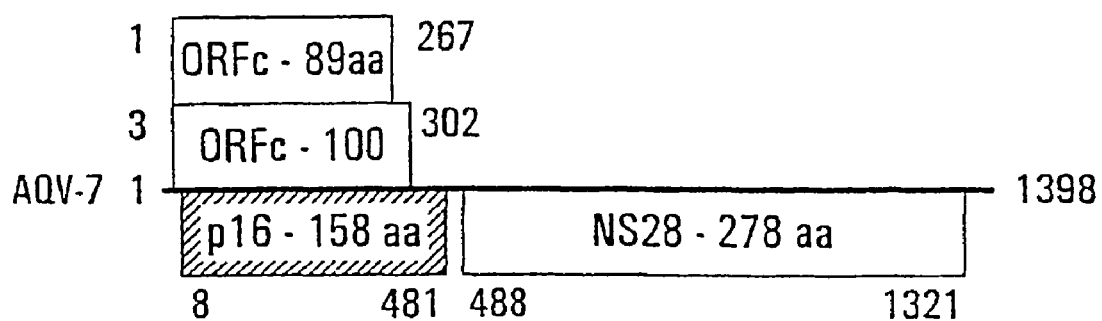
FIG. 1B presents the genome segment 7 from aquareovirus (AQV). The heavy line in each figure indicates the cDNA. Boxed areas represent open reading frames (ORFs). The ORFs are identified by the name of the ORF or the encoded gene product (within the box), and the number of amino acid codons in the particular ORF. Small numbers refer to the first and last nucleotides of the cDNA or of the indicated ORF. The ORFs encoding the membrane fusion proteins are hatched.

(A) Proteins

A class of proteins, exemplified by the p14 protein from RRV and the p16 protein from AQV, have been identified. The proteins have membrane fusion properties. Accordingly, this class of proteins, including p14, p16 and related polypeptides, can be used to promote membrane fusion.

In one aspect of the invention, proteins are provided which are encoded by the genome of Reoviridae, and whose amino acid sequence is free of fusion peptide motifs.

The family Reoviridae includes the genus *Orthoreovirus*, which includes avian, mammalian and reptilian reoviruses, as well as the genus *Aquareovirus*.

Fusion peptide motifs, as defined in the present invention, are of two classes: type I and type II. Type I is found typically in fusion proteins from enveloped proteins. Motif type I consists of an amino acid sequence 16 to 36 residues long, preferably 17 to 28 residues long, with a hydrophobicity of about 0.5 to 0.8, preferably about 0.6 to 0.7, and has a content of alanine plus glycine of about 24 to 44%, preferably 29 to 43%.

Motif type II is an atypical motif. It is found in the type of fusion protein exemplified by the p10 protein of ARV and NBV. It consists of an amino acid sequence 15 to 20 residues long, preferably 16 to 18 residues long, with a hydrophobicity value about 0.2 to 0.4, preferably about 0.3 to 0.4, has an alanine plus glycine content of about 24 to 44%, preferably about 29 to 43%; and contains at least one heptad repeat.

In accordance with the present invention, a heptad repeat is a seven-residue sequence in which residues at positions 1 and 4 are apolar. The conserved apolar first and fourth residues are thought to form part of the hydrophobic face of amphipathic helices; thus, in proteins containing them, they are likely to be an essential element for interaction between the fusion protein and the membrane.

Hydrophobicity values are determined according to methods known in the art. According to the present invention, the values are calculated using the normalized hydrophobicity scale of Eisenberg. (1984). Ann. Rev. Biochem. 53:595-623.

By "polypeptide" or "protein" is meant any chain of amino acids, regardless of length or post-translational modification (e.g., glycosylation or phosphorylation). Both terms are used interchangeably in the present application.

In another aspect of the invention, proteins are provided which are membrane fusion proteins whose amino acid sequences are free of any fusion peptide motifs, as defined above, and which are related to Reoviridae in that they comprise an amino acid sequence which has at least 33% overall identity with the membrane fusion protein encoded by Reoviridae. The proteins also comprise a transmembrane domain whose amino acid sequence has at least 60% amino acid sequence identity to the transmembrane domain of the membrane fusion protein encoded by Reoviridae. The overall percent identity is also contemplated at least 40%, 45%, 50%, 60%, and 75%. The percent identity with the transmembrane domain is also contemplated at least 70%, 75%, 80%, 85%, 90% and 95%.

In one aspect, proteins of the invention are related to Reoviridae in that the proteins comprise an amino-acid sequence which has at least 33% overall identity with the membrane fusion protein encoded by Reoviridae. The 33% overall identity is based on the degree of identity between the p10 proteins of ARV (strains 176 and 138) and of NBV.

As a class, it is clear that the proteins of the invention tolerate a great deal of sequence variation while retaining their membrane fusion properties. The membrane fusion proteins derived from Reoviridae are thus related by function and by overall structure, rather than by strict overall identity. The proteins are functionally defined in that they have membrane fusion properties which can be readily determined using a simple test. One such test is that exemplified in Examples 4 and 8, where the protein which is to be tested for membrane fusion activity is expressed in cells and the cells examined under the microscope for syncytium formation.

The proteins of the invention are structurally defined in that they are either encoded by Reoviridae, or are related to Reoviridae fusion proteins mainly at the transmembrane domain. Transmembrane domains are readily recognized in the art. A typical transmembrane domain is described in White, Annu. Rev. Physiol., 52:675-697 (1990), as a contiguous sequence of amino acids averaging 29 residues, with average hydrophobicity of 0.7±0.09 and an alanine+glycine content of 16%±8%.

In one embodiment, the proteins of the invention are encoded by, or related to, the genome of *Orthoreovirus* or *Aquareovirus* or the genome of a reovirus which naturally infects a poikilothermic (cold-blooded) host. *Orthoreovirus* includes the avian and mammalian reoviruses. *Aquareovirus* are reoviruses which naturally infect fish. Poikilothermic hosts include reptiles such as snakes, pythons and fish.

Specifically, one embodiment is directed to proteins comprising an amino acid sequence of SEQ ID NO:2 or SEQ ID NO:6. In another embodiment, the proteins of the invention are membrane fusion proteins whose amino acid sequences are free of any fusion peptide motif, as defined above, and which are related to *Orthoreovirus* or *Aquareovirus* in that they comprise an amino acid sequence which has at least 33% overall identity to the membrane fusion protein encoded by *Orthoreovirus* or *Aquareovirus*, and comprise a transmembrane domain whose amino acid sequence has at least 60% amino acid sequence identity to the transmembrane domain of the membrane fusion protein encoded by *Orthoreovirus* or *Aquareovirus*. The overall percent identity is also contemplated at least 40%, 45%, 50%, 60%, and 75%. The percent identity with the transmembrane domain is contemplated also at least 70%, 75%, 80%, 85%, 90% and 95%.

The precise N-terminus of p16 (SEQ ID NO:6) has not been determined. However, the N-terminal residue has been shown to be located within the first 17 residues of SEQ ID NO:6. Although precise identification of the initiator codon is not essential to the present invention, the initiator can be readily determined using methods known in the art. For example, a stop codon can be inserted systematically into the first 17 codons, as explained in Example 5. Alternatively, p16 can be isolated from cells in which it is expressed, and its N-terminal region micro-sequenced.

In another embodiment, the membrane fusion proteins of the invention are neutral or basic; i.e. their isoelectric point (pI) is equal to or greater than 7, preferably greater than 8, and more preferably greater than 9. The pI of a protein can be readily determined using standard methods known in the art.

In another embodiment, the proteins of the invention further comprise a positive cluster which consists of at least three, preferably four, more preferably six, most preferably seven, positively charged amino acid residues within a contiguous sequence of at most 25, preferably 23, more preferably 21, and most preferably 20 residues, wherein the contiguous sequence is within at most 100, preferably at most 90, and more preferably at most 80, residues flanking the transmembrane domain at the C-terminal side.

In another embodiment, the proteins of the invention further comprise a non-transmembrane domain which comprises a polyproline motif comprising at least 3, preferably 4, and more preferably 5 contiguous proline residues. In a specific embodiment, the fusion protein of the invention which comprises the polyproline motif is related to the p14 protein.

In another embodiment, the proteins of the invention further comprise a fatty acylation sequence, preferably a myristylation consensus sequence which is: (initiator Met removed) SEQ ID NO:9 Gly1-AA2-AA3-AA4-AA5-AA6-AA7-AA8-, where AA2, AA3, AA4, AA5, AA6 are small uncharged residues, AA3 and AA4 are preferably neutral, where AA5 is preferably serine or threonine, where AA6 is not proline, and where AA7 and AA8 are preferably basic (Towler et al. Annu. Rev. Biochem. 57:69-99 (1988); Resh. Biochim. Biophys. Acta. 1451:1-16 (1999)). In a specific embodiment, the fusion protein of the invention which comprises the fatty acylation sequence is related to the p14 protein.

As described herein, the invention also encompasses substantially purified proteins. A "substantially purified protein" as used herein is defined as a protein that is separated from the environment in which it naturally occurs and/or that is free of the majority of the proteins that are present in the environment in which it was synthesized. For example, a substantially purified protein is free from cytoplasmic proteins. Those skilled in the art would readily understand that the proteins of the invention may be purified from a natural source, i.e., a Reoviridae-infected cell, or produced by recombinant means.

Useful derivatives of the membrane fusion proteins of the invention, e.g., fusion-promoting fragments, may be designed using computer-assisted analysis of amino acid sequences to identify probable transmembrane regions, or regions of high positive charge. Parameters such as helix propensity, heptad repeats and average hydrophobicity can reveal potential hydrophobic, membrane-interacting fragments which may be used as a basis for selecting useful fusion-promoting fragments and variants.

One aspect of the invention provides sequences that are identical or substantially identical to SEQ ID NOs: 2, 4, 6 and 8. By "amino acid sequence substantially identical" is meant a sequence that is at least 80%, preferably 90%, more preferably 95% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, proline, phenylalanine, methionine, tryptophan, and cysteine.

Percent identity is measured using sequence analysis software such as the Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of identity is established by recording all of the positions in which the amino acids of both sequences are identical, relative to the total number of positions.

Proteins having a sequence homologous to SEQ ID Nos: 2, 4, 6 or 8 include naturally-occurring allelic variants, as well as mutants or any other non-naturally occurring variants that retain the membrane fusion properties of the polypeptides of SEQ ID Nos: 2, 4, 6 or 8. As is known in the art, an allelic variant is an alternate form of a polypeptide that is characterized as having a substitution, deletion, or addition of one or more amino acids that retain the biological function of the polypeptide, i.e. the membrane-fusion activity.

Homologs and fragments thereof that do not occur naturally are designed using known methods for identifying regions of the protein that are likely to tolerate amino acid sequence changes and/or deletions. As an example, homologous polypeptides from different species are compared; conserved sequences are identified. The more divergent sequences are the most likely to tolerate sequence changes. Percent identity and similarity among sequences may be analyzed using, as an example, the BLAST homology searching algorithm of Altschul et al., Nucleic Acids Res. 25:3389-3402 (1997). Alternatively, a particular amino acid residue or sequence within the polypeptide can be mutated in vitro, then the mutant polypeptides screened for their ability to promote membrane fusion.

A skilled person will understand that by following the screening process of this invention, it will be determined without undue experimentation whether a particular protein encoded by Reoviridae, or related to a protein encoded by Reoviridae, has membrane fusion activity. The screening procedure comprises the steps:

(i) Introducing the test protein into a cell susceptible to syncytia formation, either by delivering the protein or by expressing the protein from a polynucleotide encoding it; and (ii) Observing whether membrane fusion has occurred by determining whether syncytia have formed, compared to a negative control where an irrelevant protein is introduced into the cell.

(B) Antibodies

One aspect of the invention provides antibodies, both polyclonal and monoclonal. Such antibodies can be employed for diagnostic applications, therapeutic applications, and the like. Preferably, for therapeutic applications, the antibodies employed will be monoclonal antibodies. Antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

Antibodies against the proteins or fragments of the invention are generated by immunization of a mammal with a composition comprising the protein or fragment. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657-680.

Polyclonal antibodies may be obtained, for example, by immunizing three month old male and female white New Zealand rabbits with the synthetic peptide to which Tyr has been added at the C-terminus in order to couple it, as an antigen, to BSA by a bisdiazotized benzidine (BDB) linkage by reaction for 2 hours at 4° C. The reaction mixture is dialyzed to remove low molecular weight material, and the retentate is frozen in liquid nitrogen and stored at −20° C. Animals are immunized with the equivalent of 1 mg of the peptide antigen according to the procedure of Benoit et al. P.N.A.S. USA, 79, 917-921 (1982). At four week intervals, the animals are boosted by injections of 200 ug of the antigen and bled ten to fourteen days later. After the third boost, antiserum is examined for its capacity to bind radioiodinated antigen peptide prepared by the chloramine-T method and then purified by CMC-ion exchange column chromatography. The antibody molecules are then collected from the mammal and isolated to the extent desired by well known techniques such as, for example, by using DEAE-Sephadex to obtain the IgG fraction.

For monoclonal antibodies, see Kohler & Milstein (1975) Nature 256:495-497. In general, procedures for preparing monoclonal antibodies involve immunizing an animal with the protein or fragment (the 'antigen'). The splenocytes of such animals are extracted and fused with a suitable myeloma cell line. After fusion, the resulting hybridoma cells are selectively maintained in HAT medium, and then cloned as described in Wands et al. Gastro-enterology. 80:225-232 (1981). The hybridoma cells obtained through such a selection are then assayed to identify clones which secrete antibodies capable of binding the antigen.

To enhance the specificity of the antibody, the antibodies may be purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

A radioimmunoassay is established with the antisera and serum from subsequent bleeds from the same rabbits. The native protein is recognized by the antibodies on an equimolar basis as compared to the synthetic peptide antigen.

The antibody so produced can be used, inter alia, in diagnostic methods and systems to detect the level of fusion protein present in a test sample. In addition, anti-fusion protein antibodies can be used in therapeutic methods, e.g., blocking the occurrence of undesired fusion processes. The anti-fusion protein antibodies can also be used for the immunoaffinity or affinity chromatography purification of such fusion proteins.

Accordingly, one aspect of the invention provides a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody is either polyclonal or monospecific, and preferably is of the IgG type. Purified IgG is prepared from an antiserum using standard methods (see, e.g., Coligan et al., Current Protocols in Immunology (1994) John Wiley & Sons, Inc., New York, N.Y.). Conventional chromatography supports, as well as standard methods for grafting antibodies, are described in, e.g., Antibodies: A Laboratory Manual, D. Lane, E. Harlow, Eds. (1988) and outlined below.

Briefly, a biological sample, such as a cell extract containing the membrane fusion protein, preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g., guanidine HCl, or high salt concentration (e.g., 3M MgCl2). Eluted fractions are recovered and the presence of the antigen is detected, e.g., by measuring the absorbance at 280 nm.

(C) Polynucleotides, their Expression and Use

According to one aspect of the invention, isolated polynucleotides are provided which encode the membrane fusion proteins of the invention. In one embodiment, the polynucleotides are those of SEQ ID NOs: 1 and 5.

The term "isolated polynucleotide" is defined as a polynucleotide removed from the environment in which it naturally occurs. For example, a naturally-occurring DNA molecule present in the genome of a living virus or as part of a gene bank is not isolated, but the same molecule separated from the remaining part of the viral genome, as a result of, e.g., a cloning event (amplification), is isolated. Typically, an isolated polynucleotide molecule is free from polynucleotide regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotide of the invention is either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. Any one of the sequences that encode the proteins of the invention as shown in SEQ ID No: 2, 4, 6 and 8 is (a) a coding sequence, (b) a ribonucleotide sequence derived from transcription of (a), or (c) a coding sequence which uses the redundancy or degeneracy of the genetic code to encode the same polypeptides.

Homologous polynucleotide sequences are defined in a similar manner to homologous amino acid sequences. Preferably, a homologous polynucleotide sequence is one that is at least 45%, more preferably 60%, and most preferably 85% identical to sequence encoding the proteins of the invention, or to the coding sequences of SEQ ID NOs 1 and 5, or to the sequence encoding the proteins of SEQ ID NOs:2, 4, 6 and 8.

Polynucleotides encoding homologous polypeptides or allelic variants are retrieved by polymerase chain reaction (PCR) amplification of genomic viral polynucleotides extracted by conventional methods; (see Example 2). This involves the use of synthetic oligonucleotide primers matching upstream and downstream of the 5' and 3' ends of the coding region. Suitable primers are designed according to the nucleotide sequence information provided in SEQ ID Nos:1 and 5. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 μL, 20 to 200 μM deoxynucleotide each, preferably at equivalent concentrations, 0.5 to 2.5 mM magnesium over the total deoxynucleotide concentration, 105 to 106 target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for dematuration of G+C-rich targets. The number of cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: $Tm=81.5+0.41\times(\% G+C)+16.6\log(\text{cation ion concentration})-0.63\times(\% \text{formamide})-600/\text{base number}$. Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

Polynucleotide molecules according to the invention, including RNA, DNA, or modifications or combinations thereof, have various applications. A DNA molecule is used, for example, (i) in a process for producing the encoded polypeptide in a recombinant host system, (ii) as part of a gene delivery system, e.g. liposomes, which, upon delivery, becomes expressed and promote membrane fusion, (iii) operably linked to regulatory elements as part of an expression cassette which, when turned on, expresses the polynucleotide and promote membrane fusion, and, (iv) as a probe or primer.

Accordingly, one aspect of the invention encompasses (i) an expression cassette containing a polynucleotide of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic host cell transformed or transfected with an expression cassette and/or vector of the invention, under conditions that allow expression of the DNA molecule of the invention without being toxic to the host cell and, recovering the encoded polypeptide or polypeptide derivative from the host cell culture.

A recombinant expression system is selected from procaryotic and eucaryotic hosts. Since the proteins of the invention promote membrane fusion, host cells are selected which can be maintained and which can express the proteins within tolerable limits of toxicity. Eucaryotic hosts include yeast cells (e.g., *Saccharomyces cerevisiae* or *Pichia pastoris*), plant cells, and cells which preferably have a cell wall so that the integrity of the host cell is not affected by the fusion activity. A preferred expression system is a procaryotic host such as *E. coli*. Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

One skilled in the art would readily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen such that it is not affected by the fusion activity of the expressed membrane fusion protein. In addition, a host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variables are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are: compatible with the selected vector, tolerant of any possible toxic effects of the expressed product, able to express the product efficiently, able to express the product in the desired conformation, easily scaled up, and easy to use for purifying the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide; a polynucleotide of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system.

Promoters and signal peptide encoding regions are widely known and available to those skilled in the art and include, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., Protein Engineering (1991) 4(7):843)); the promoter of the gene of bacteriophage T7 encoding RNA polymerase, that is functional in a number of *E. coli* strains expressing T7 polymerase (described in U.S. Pat. No. 4,952, 496); OspA lipidation signal peptide; and RlpB lipidation signal peptide (Takase et al., J. Bact. (1987) 169:5692).

Promoters contemplated for use herein include inducible (e.g., minimal CMV promoter, minimal TK promoter, modified MMLV LTR), constitutive (e.g., chicken alpha-actin promoter, MMLV LTR (non-modified), DHFR), and/or tissue specific promoters.

Inducible promoters contemplated for use in the practice of the present invention comprise transcription regulatory regions that function maximally to promote transcription of mRNA under inducing conditions. Examples of suitable inducible promoters include DNA sequences corresponding to: the *E. coli* lac operator responsive to IPTG (see Nakamura et al., Cell, 18:1109-1117, 1979); the metallothionein promoter metal-regulatory-elements responsive to heavy-metal (e.g., zinc) induction (see Evans et al., U.S. Pat. No. 4,870, 009), the phage T7lac promoter responsive to IPTG (see Studier et al., Meth. Enzymol., 185: 60-89, 1990; and U.S. Pat. No. 4,952,496), the heat-shock promoter; the TK minimal promoter; the CMV minimal promoter; a synthetic promoter; and the like.

The expression cassette is typically part of an expression vector, which is selected for its ability to replicate in the chosen expression system. Expression vectors (e.g., plasmids or viral vectors) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Ausubel et al., Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained as described below.

The sequence information provided in the present application enables the design of specific nucleotide probes and primers that are used for diagnostic purposes. Accordingly, one aspect of the invention provides a nucleotide probe or primer having a sequence found in or derived by degeneracy of the genetic code from a coding sequence shown in SEQ ID No:1 or 5.

A primer is a probe of usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art.

In one embodiment, optionally labeled cDNAs encoding fusion proteins, or fragments thereof, can be employed to probe library(ies) (e.g., cDNA, genomic, and the like) for additional sequences encoding novel fusion proteins. Such screening is typically initially carried out under low-stringency conditions, which comprise a temperature of less than about 0.42° C., a formamide concentration of less than about 50%, and a moderate to low salt concentration. Presently preferred screening conditions comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect identity for the identification of a stable hybrid. The phrase "substantial similarity" refers to sequences which share at least 50% identity. Preferably, hybridization conditions will be selected which allow the identification of sequences having at least 70% identity with the probe, while discriminating against sequences which have a lower degree of identity with the probe.

As used herein, a nucleic acid "probe" is single-stranded DNA or RNA, or analogs thereof, that has a sequence of nucleotides that includes at least 14, preferably at least 20, more preferably at least 50, contiguous bases that are the same as (or the complement of) any 14 or more contiguous bases set forth in any of SEQ ID NO:1 or 5. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in a nucleic acid probe, an expressed protein, polypeptide fragment, or antibody molecule that is part of an antibody or monoclonal antibody composition of the present invention, or used separately. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalene-sulfonyl chloride (DANSC), tetramethylrhodamine isothiocyanate (TRITC), lissamine, rhodamine 8200 sulphonyl chloride (RB-200-SC), and the like. A description of immunofluorescence analysis techniques is found in DeLuca, "Immunofluorescence Analysis", in Antibody As a Tool, Marchalonis et al., Eds., John Wiley & Sons, Ltd., pp. 189-231 (1982).

In preferred embodiments, the indicating group is an enzyme, such as horseradish peroxidase (HRP), glucose oxidase, and the like. In such cases where the principal indicating group is an enzyme, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which emit gamma rays, such as 124I, 125I, 126I, 131I and 51Cr, represent one class of radioactive element indicating groups. Particularly preferred is 125I. Another group of useful labeling means are those elements such as 11C, 18F, 15O and 13N which emit positrons. The positrons so emitted produce gamma rays upon encounters with electrons present in the animal's body. Also useful is a beta emitter, such as 32P, 111In or 3H.

The linking of labels to substrate, i.e., labeling of nucleic acid probes, antibodies, polypeptides, and proteins, is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas et al., Scand. J. Immunol., Vol. 8, Suppl. 7:7-23 (1978), Rodwell et al., Biotech., 3:889-894 (1984), and U.S. Pat. No. 4,493,795.

(D) Compositions Containing Membrane Fusion Proteins and Polynucleotides

As used herein, the composition of the invention contains one or several membrane fusion proteins or derivatives of the invention.

For use in a composition of the invention, according to one embodiment, a membrane fusion protein or derivative thereof is formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach, RCP New Ed, IRL press (1990).

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for drug or gene delivery. Such lipids include Lipofectin™ also known as DOTMA (N-[1-(2,3-dioleyloxy)propyl]-N,N,N-trimethylammonium chloride), DOTAP (1,2-bis(oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, Wo 90/11092, U.S. Pat. No. 5,283,185, WO 91/15501, WO 95/26356, and U.S. Pat. No. 5,527,928. Cationic lipids for delivery of polynucleotides are preferably used in association with a neutral lipid such as DOPE (dioleyl phosphatidylethanolamine), as described in WO 90/11092 as an example.

Formulations containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

The present invention also contemplates therapeutic compositions containing a physiologically tolerable carrier together with a fusion protein, polypeptide fragment thereof, or anti-fusion protein antibody, as described herein, dissolved or dispersed therein as an active ingredient.

As used herein, the terms "pharmaceutically acceptable", "physiologically tolerable" and grammatical variations thereof, as they refer to compositions, carriers, diluents, and reagents, are used interchangeably and represent that the materials are capable of administration to a mammal without the production of undesirable physiological effects such as nausea, dizziness, gastric upset, and the like.

Methods for the preparation of a pharmacological composition that contains active ingredients dissolved or dispersed therein is well known in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients that are pharmaceutically acceptable and compatible with the active ingredient and in amounts suitable for use in the therapeutic methods described herein. Suitable excipients are, for example, water, saline, dextrose, glycerol, ethanol, or the like, as well as combinations thereof. In addition, if desired, the composition can contain minor amounts of auxiliary substances such as wetting or emulsifying agents, pH buffering agents, and the like, which enhance the effectiveness of the active ingredient.

The therapeutic composition of the present invention can include pharmaceutically acceptable salts of the components therein. Pharmaceutically acceptable nontoxic salts include the acid addition salts (formed with the free amino groups of the polypeptide) that are formed with inorganic acids such as, for example, hydrochloric acid, hydrobromic acid, perchloric acid, nitric acid, thiocyanic acid, sulfuric acid, phosphoric acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, and the like.

Salts formed with the free carboxyl groups can also be derived from inorganic bases such as, for example, sodium hydroxide, ammonium hydroxide, potassium hydroxide, and the like; and organic bases such as mono-, di-, and tri-alkyl and aryl amines (e.g., triethylamine, diisopropyl amine, methyl amine, dimethyl amine, and the like), and optionally substituted ethanolamines (e.g., ethanolamine, diethanolamine, and the like).

Physiologically tolerable carriers are well known in the art. Exemplary liquid carriers are sterile aqueous solutions that contain no materials other than the active ingredients and water, or contain a buffer such as sodium phosphate at physiological pH value, physiological saline, or both, such as phosphate-buffered saline. Still further, aqueous carriers can contain more than one buffer salt, as well as salts such as sodium and potassium chlorides, dextrose, polyethylene glycol, and other solutes.

Liquid compositions can also contain liquid phases in addition to and to the exclusion of water. Exemplary of such additional liquid phases are glycerin, vegetable oils such as cottonseed oil, and water-oil emulsions.

A therapeutically effective amount is a predetermined amount calculated to achieve the desired effect. The required dosage will vary with the particular treatment and with the duration of desired treatment; however, it is anticipated that dosages between about 10 micrograms and about 1 milligram per kilogram of body weight per day will be used for therapeutic treatment. In some instances, it may be particularly advantageous to administer such compounds in depot or long-lasting form. A therapeutically effective amount is typically an amount of a fusion protein according to the invention, or polypeptide fragment thereof that, when administered in a physiologically acceptable composition, is sufficient to achieve a plasma concentration of from about 0.1 µg/ml to about 100 µg/ml, preferably from about 1.0 µg/ml to about 50 µg/ml, more preferably at least about 2 µg/ml and usually 5 to 10 µg/ml. Antibodies are administered in proportionately appropriate amounts in accordance with known practices in this art.

(E) Methods of Use

One aspect of the invention provides methods of using the proteins, polynucleotides and compositions of the invention. Accordingly, methods are provided to promote membrane fusion which comprise contacting the membranes to be fused with an effective amount of the above-described proteins.

Membranes contemplated for fusion in accordance with the present invention include cell membranes, liposome membranes, proteoliposome membranes, and the like.

In accordance with a still further embodiment of the present invention, there are provided methods for the production of heterokaryons, such as B cell or T cell hybridoma cells useful for the production of monoclonal antibodies, cytokines, and immune modulators, said methods comprising contacting, for example, an immortalized myeloma cell and a primary B cell or T cell in the presence of any one or more of the above-described proteins. Immortalized cells contemplated for use herein include human or mouse B cell myeloma cells, T cell myelomas, and the like, and antibody-synthesizing cells contemplated for use herein include purified spleen cells from an immunized mammal, and the like.

In accordance with a still further embodiment of the present invention, there are provided methods for the production of liposome-liposome fusions or liposome-cell fusions, said methods comprising contacting lipids suitable for the formation of liposomes and a suitable cell in the presence of one or more proteins as described herein.

In accordance with yet another embodiment of the present invention, there are provided improved methods for the intracellular delivery of bioactive compounds employing liposomes, the improvement comprising incorporating into said liposomes one or more proteins as described herein.

The ability to promote efficient membrane fusion has broad applicability in clinical, industrial, and basic research situations. The reovirus fusion proteins could be used as alternatives to chemically-induced membrane fusion to promote cell-cell fusion, for example, during the production of hybridoma cells for monoclonal antibody production. In this instance, the reovirus fusion proteins would be inducibly expressed from inside a transiently or permanently transfected cell population to trigger fusion of these cells with a target cell population.

The atypical reovirus fusion proteins also have application in enhancing liposome-cell fusion. Liposomes have been developed as a means to introduce nucleic acids, proteins, and metabolic regulators into cells. Although liposome-cell fusion has been amply demonstrated, the unfavourable thermodynamics of membrane fusion contribute to variable efficiencies of fusion and cytotoxicity which lead to the development of proteoliposomes—liposomes containing specific proteins to promote cell binding and fusion.

Most of the proteoliposome studies reported in the art relate to the use of various enveloped virus fusion proteins. In accordance with the present invention, it is possible to take advantage of the novel structural features associated with the invention reovirus fusion proteins for use in proteoliposomes to enhance the intracellular delivery of bioactive compounds (e.g., nucleic acids, proteins or peptides, pharmacological agents, and the like), both in cell culture and in vivo.

The reovirus fusion proteins described herein promote membrane fusion in a diversity of cell types (e.g., fibroblasts and macrophages) from different species (e.g., avian and mammalian, including human) suggesting limited cell receptor-specificity as well as the general applicability of these proteins. It may also be possible to target reovirus fusion protein-containing proteoliposomes to specific cell types by including specific receptor-binding proteins in the liposome membrane. In this instance, the receptor-binding protein would confer targeted cell attachment of the liposome followed by subsequent enhanced liposome-cell fusion mediated by the reovirus fusion protein.

The demonstrated ability of p14 and p16 to induce cell-cell fusion indicates their potential use in the production of heterokaryons, for example, the generation of hybridomas for monoclonal antibody production. The induction of cell-cell fusion is usually triggered using the chemical fusogen polyethylene glycol (PEG). Although this procedure does trigger cell-cell fusion, toxic effects on cells hamper the efficiency of heterokaryon isolation. It is generally believed that "natural" membrane fusion is mediated by protein-lipid interactions, therefore, protein-mediated membrane fusion is likely to be much less cytotoxic than chemically-induced cell fusion.

The demonstrated ability of the small reovirus fusion proteins to promote efficient cell-cell fusion indicates their potential use as alternatives to chemical-induced cell fusion. Expression of p14 or p16 in one population of cells, under the control of a strong inducible promoter, could trigger fusion with a second cell population, resulting in decreased cytotoxicity and more efficient heterokaryon isolation.

The atypical group of nonenveloped virus fusion proteins described herein represent alternatives to the use of enveloped virus fusion proteins in the protein-mediated enhancement of liposome-cell fusion for the intracellular delivery of bioactive molecules. The potential advantages of the reovirus fusion proteins relate to their unique structural and biological features. From a structural perspective, the small size of the reovirus fusion proteins is the most apparent advantage offered by this system. The large size, post-translational glycosylation, and complex tertiary structure of the enveloped virus fusion proteins makes synthesis and purification of the functional protein using recombinant DNA approaches and prokaryotic or eukaryotic expression systems problematic.

The majority of studies relating to the use of enveloped virus fusion proteins in proteoliposomes involve the production of virus particles which are subsequently purified, solubilized with detergent, and the viral envelopes containing the fusion protein are reconstituted into "virosomes" by removal of the detergent (see Grimaldi in Res. Virol., 146:289-293 (1995) and Ramani et al., FEBS Lett., 404:164-168 (1997)). Unlike most of the enveloped virus fusion proteins, the reovirus fusion proteins are small membrane proteins. Their small size and simple domain organization suggests that these proteins will be easier and more economical to produce in a functional form using a diversity of expression and purification protocols. It is also likely that the small size of the reovirus fusion proteins contributes to less complex protein folding pathways and tertiary structure required for correct protein conformation. As a result, an increased diversity of extraction and solubilization procedures (e.g., choice of detergents and denaturants) should be available to facilitate purification of the functional fusion protein and incorporation into liposomes.

The attractive biological properties of the reovirus fusion proteins relate to their pH-independent fusion mechanism with numerous cell types. The reovirus fusion proteins function at neutral pH, unlike the influenza virus HA protein, simplifying their use in cell culture and in vivo under physiological conditions. Furthermore, the reovirus fusion proteins fuse numerous types of cells suggesting their broad applicability as fusogens. This could include such primary cell types as dendritic cells, neurons, and stem cells which are difficult to transfect using standard transfection reagents. Accordingly, the reovirus fusion proteins could be used to promote liposome-cell fusion and the efficient intracellular delivery of DNA or other bioactive compounds into a diversity of cultured cell types, primary cell cultures, tissue explants, or in vivo.

In order to use reovirus fusion proteins for heterokaryon production, the proteins will need to be expressed in a controlled, inducible manner from within cells using standard recombinant DNA approaches. The utility of this approach has already been demonstrated in homologous cell-cell fusion in a non-inducible manner. In a similar fashion, these proteins can promote cell-cell fusion between heterologous cell types in an inducible manner.

The development of reovirus fusion proteins for enhanced liposome-cell fusion requires the expression and purification of the functional fusion proteins and their incorporation into liposome membranes to produce proteoliposomes. The p14 and p16 proteins can be expressed and purified using standard procedures. Expression can be accomplished employing a variety of expression systems, e.g., baculovirus or yeast eukaryotic expression vectors or from prokaryotic expression vectors, depending on expression levels and functional activity of the protein. Various detergent extraction procedures can be used to solubilize the proteins, which can then be purified as detergent-protein complexes using standard protein purification protocols. The proteins are readily soluble in various detergents (e.g. 0.8% Triton X100, 0.8% NP40, 0.8% octylglucoside) increasing the diversity of approaches available for functional protein purification. The small size of the reovirus fusion proteins suggests that protein solubilization and purification should be considerably more simple than similar approaches to purify larger, more complex membrane proteins.

The detergent-protein complexes can be mixed with lipids and the detergent removed by dialysis, chromatography, or extraction according to standard published procedures, similar to methods used to generate influenza HA or Sendai virus F protein-containing virosomes (see Grimaldi, Res. Virol., 146:289-293 (1995) and Ramani et al., FEBS Lett., 404:164-168 (1997)). These procedures will result in the production of proteoliposomes, lipid vesicles containing the ARV, NBV, or BRV fusion proteins embedded in the vesicle membrane. Once again, optimal conditions for proteoliposome production can be empirically determined as can the lipid composition and size of the proteoliposomes which can affect the efficiency of liposome-cell fusion. Bioactive molecules of interest (e.g., nucleic acids, proteins or peptides, pharmacological compounds, and the like) can be included during the formation of the proteoliposmes to facilitate packaging of the molecule within the liposomes. The proteoliposomes can be purified by centrifugation and used to deliver bioactive molecules intracellularly, either in cell culture or in vivo, by protein-enhanced fusion of the proteoliposomes with cell membranes.

As acknowledged above, the use of liposomes or proteoliposomes for intracellular delivery of compounds is known in the art, and development of such methodology is proceeding on several fronts. What is unique with the present system is the use of an atypical, previously unidentified group of nonenveloped virus fusion proteins isolated from the only known fusogenic poikilothermic reoviruses. The unusual structural and functional properties of this new group of fusion proteins suggest that these proteins may circumvent many of the problems associated with the current development of protein-mediated membrane fusion.

While the invention has been described in detail with reference to certain preferred embodiments thereof, it will be understood that modifications and variations are within the spirit and scope of that which is described and claimed.

EXAMPLES

Example 1

Virus Growth and Purification

Viruses were plaque purified and grown in monkey Vero cells. Virus particles were isolated and concentrated from infected cell lysates by differential centrifugation, as previously described (see Duncan, Virology, 219:179-189. (1996)).

Example 2

Synthesis and Cloning of cDNA

The viral genomic dsRNA segments were isolated from concentrated virus stocks pretreated with RNase and DNase to remove extra-virion contaminating cellular nucleic acids. Virus particles were disrupted using 1% SDS and the viral dsRNA isolated by phenol-chloroform extraction and ethanol precipitation. Aliquots of genomic dsRNA (20 ug) were poly-A-tailed using $E.$ $coli$ poly-A polymerase, the tailed RNA was fractionated by agarose gel electrophoresis, and individual genomic segments were isolated using the RNaid protocol (Bio101) according to the manufacturers specified procedure.

The tailed S class genome segments were used as templates for reverse transcription, using Superscript reverse transcriptase (Life Technologies Inc.) and an oligo-dT primer. Aliquots of the plus and minus strand cDNAs were used as templates for PCR amplification using Vent polymerase (New England Biolabs) and an oligo-dT primer containing a NotI restriction enzyme site.

The products of the PCR reaction were digested with NotI, size-fractionated on agarose gels, and products corresponding to the full length S genome segments were gel-purified using Geneclean (Bio101). The individual, NotI-digested, double-stranded cDNAs were cloned into the NotI site of pBluescript (Stratagene) and used as templates for sequencing.

Example 3

Sequencing and Sequence Analysis

The cloned cDNAs were sequenced using an automated DNA sequencer (Licor) at the NRC/Dalhousie Joint Sequencing Core Facility. All sequences were determined in their entirety from both cDNA strands. The full length cDNA sequences were compiled and analyzed using the GCG sequence analysis software (see Devereaux et al., Nucleic Acids Res., 12:387-395 (1984)).

Example 4

Identification of Genome Segments Encoding the Fusion Proteins of RRV and AQV

The RRV and AQV cDNA clones were subcloned into the eukaryotic expression vector pcDNA3 (Invitrogen) under the control of the CMV promoter. Plasmid DNA was isolated and purified on Qiagen midi columns (Qiagen) according to the manufacturer's specifications. Plasmid DNA (1 ug) was mixed with Lipofectamine (3 ul) (Life Technologies Inc.) and used to transfect sub-confluent cell monolayers grown in 12 well cluster plates. Transfected cell monolayers were incubated at 37° C. for 24-48 hr before being fixed with methanol and stained using a water-soluble Wright-Giemsa stain (Dif-fQuik; VWR-Canlab), as previously described (see Duncan et al., Virology, 224:453-464 (1996)). Cell fusion was assessed by light microscopy of stained monolayers and syncytial foci were photographed at 100× magnification. Using this protocol, the S1 genome segment of RRV and genome segment 7 of AQV were determined to encode the fusion proteins of these viruses.

Example 5

Identification of p14 and p16 Fusion Proteins

Two unrelated fusion proteins responsible for the cell-cell fusion induced by reptilian reovirus (RRV) and aquareovirus (AQV) have been identified. These proteins are referred to herein as p14 (for RRV) and p16 (for AQV) to reflect their approximate predicted molecular weights. The genes encoding p14 and p16 have been cloned and sequenced. The sequence-predicted structural organization of these proteins has been analyzed, and the membrane fusion properties thereof have been directly demonstrated. The organization of the RRV S1 genome segment and the AQV genome segment 7 are indicated diagrammatically in FIG. 1 and the cDNA sequences and predicted translation products are shown in FIGS. 2-5 (SEQ ID Nos:1-6).

p14 of Reptilian Reovirus:

Sequence analysis determined that the RRV S1 genome segment is 1501 base pairs long and contains the conserved terminal nucleotide sequences 5'-GTTA . . . TCATC-3' present in other RRV genome segments, indicating the sequence represents the full-length cDNA sequence of the S1 genome segment. This represents the first nucleotide sequence reported for any genome segment of any reptilian reovirus.

Sequence analysis revealed the presence of two sequential overlapping ORFs. Based on sequence similarity, the second ORF spanning nucleotides 386-1432 (including the ATG start codon and excluding the termination codon) encodes the 349 amino acid homolog of the typical reovirus cell attachment protein, termed sigma C for avian reovirus and sigma 1 for mammalian reovirus (Shapouri et al., J. Gen. Virol., 76:1515-1520).

The first ORF, spanning nucleotides 25-399, encodes a previously unidentified predicted 125 amino acid protein. The predicted 125 amino acid product of the first ORF had no homolog amongst the known reovirus proteins, and displayed no significant sequence similarity to any proteins contained in the databanks. The first ORF was subcloned by PCR using specific primers into pcDNA3. Expression of the first ORF alone in transfected cells resulted in cell-cell fusion (see Example 8) indicating that RRV encodes a novel 14 Kda fusion protein, termed p14.

p16 of *Aquareovirus:*

The AQV genome segment 7 sequence was found to be 1398 base pairs long and contained the conserved terminal nucleotide sequences 5'-GTTT . . . TCATC-3' present in other AQV genome segments, indicating the sequence represents the full-length cDNA sequence of genome segment 7. This is the first nucleotide sequence reported for genome segment 7 of any aquareovirus.

Sequence analysis revealed a complex arrangement of ORFs on the AQV genome segment 7. The first methionine start codon does not occur until 488 nucleotides from the 5'-end of the gene. This start codon is followed by a single ORF encoding a predicted 278 amino acid protein, presumably the previously identified NS28 protein, the only known gene product of this genome segment (Subramanian et al., Virology, 205:75-81 (1994)). In the 5'-terminal 487 nucleotides preceding this start codon, all three reading frames contain ORFs. The ORF in reading frame "a" spans nucleotides 1-267, the ORF in reading frame "b" spans nucleotides 8-481, and the ORF in reading frame "c" spans nucleotides 3-302. Each of these ORFs lack a conventional ATG start codon, but could conceivably be functional using a codon other than methionine as a start codon, as occurs, for example, with the C proteins encoded by the P mRNA of Sendai virus (see Curran and Kolakofsky, EMBO J., 7:245-251 (1988)). These AQV ORFs can encode 89, 158, or 100 amino acid proteins for reading frames a, b, and c, respectively.

The 5'-terminal 484 nucleotides of the AQV genome segment 7 were subcloned into pcDNA3 by PCR amplification using specific primers, expressed in transfected cells, and found to induce cell-cell fusion. This result confirms that the AQV fusion protein was encoded by one of the three predicted small ORFs present near the 5'-end of the genome segment.

Of the three possible gene products encoded by this region, only the potential 158 amino acid product of reading frame b, termed p16, was predicted to be a membrane localized protein, as would be expected for a protein capable of causing membrane fusion (two transmembrane regions are predicted to exist in p16, as determined using the TMpred and PSORT algorithms; see Example 7). In order to confirm that p16, encoded by the second ORF, represents the AQV fusion protein, site-directed mutagenesis was used to insert a C to T substitution at position 59. This substitution introduces a translation stop site into reading frame b specifically, which would result in the premature termination of the p16 ORF after only 17 codons. Such a substitution eliminated cell fusion, confirming that the predicted p16 gene product of ORF b represents the AQV fusion protein. Since the p16 ORF lacks the typical methionine start codon, the precise start site of p16 is not presently known but clearly resides in one of the 17 codons that occur upstream of the nucleotide substitution used to engineer a stop codon at position 59.

Example 6

Sequence Analysis of p14

The RRV p14 fusion protein is one of the smallest known fusion proteins at only 125 amino acids in length. It shares no significant sequence similarity with any protein in the databases, including those implicated as membrane fusion proteins such as the enveloped virus fusion proteins, the cellular SNARE proteins, or even the previously identified fusion proteins of avian reovirus and Nelson Bay reovirus (Shmulevitz and Duncan, EMBO J., 19:902-912 (2000), White, Annu. Rev. Physiol., 52:675-697 (1990), Weber et al., Cell, 92:759-772 (1998)). As such, p14 represents a novel membrane fusion protein.

The p14 protein contains a single predicted transmembrane domain, detected using both the TMpred and PSORT algorithms, located between residues 39-57 (see FIG. 4). It also contains an N-terminal myristylation consensus sequence (MGXXXS/T) suggesting the protein may be acylated. Sequence analysis also detected a cluster of basic residues on the C-proximal side of the transmembrane domain, and a polyproline motif and N-linked glycosylation consensus sequence (NXS/T) located near the C-terminus of the protein (see FIG. 4).

Interestingly, p14 lacks an obvious fusion peptide, a small stretch of hydrophobic amino acids located in the extracellular domain of enveloped virus fusion proteins and involved in insertion of a fusion protein into the target membrane. Moreover, the p14 protein lacks any apparent heptad repeats required for the coiled coil rearrangements observed in enveloped virus fusion proteins. The lack of fusion peptide and heptad repeat motifs in p14 suggests that p14 may promote membrane fusion through a mechanism distinct from that proposed for the well described enveloped virus fusion proteins (see White, Ann. Rev. Physiol., 52:675-697 (1990)).

Example 7

Sequence Analysis of p16

The AQV p16 fusion protein shares no obvious sequence homology with either the RRV p14 fusion protein, the fusion proteins of avian reovirus or Nelson Bay reovirus, or any other protein in the databases. The p16 protein is approximately 158 amino acids in size. The precise size is not known and depends on which of the 17 N-terminal codons present in the p16 ORF serve as the start codon for this protein. Unlike p14, the p16 protein has two predicted transmembrane domains located approximately between residues 35-57 and 92-110. This configuration of transmembrane domains suggests an unusual polytopic membrane orientation for p16. As with p14, p16 contains clusters of basic residues adjacent to the transmembrane domains and p16 also lacks obvious fusion peptide and heptad repeat motifs.

Example 8

The p14 and p16 Fusion Proteins Induce Cell-Cell Fusion

The fusion-inducing potential of these reovirus proteins has been directly demonstrated by expressing them in transfected cells in the absence of any other reovirus proteins; intracellular expression triggers the induction of cell-cell fusion and syncytium formation characteristic of virus infection by this group of fusogenic reoviruses. Thus, quail or Vero cell monolayers were mock transfected, or transfected with plasmid DNA expressing the RRV or AQV fusion proteins. Transfected cells were fixed and the nuclei stained using a Wright-Giemsa stain at 24 hr post infection and the stained monolayers were photographed at 100× magnification.

Transfection of plasmids expressing either RRV p14 or AQV p16 resulted in extensive cell fusion and the development of multinucleated syncytia (polykaryons). The appearance of polykaryons was evident when transfected cells were stained to display the cell nuclei, which clearly showed the clustering of nuclei within large syncytial cells. Mock transfected cells showed no signs of syncytium formation, indicating that cell fusion was the direct result of the expression of the reovirus proteins within transfected cells. These results conclusively demonstrate the membrane fusion-inducing capability of the reovirus fusion proteins of the invention.

Transfection of other reovirus proteins fails to induce cell fusion, indicating that this is a p14- or p16-specific event. In addition, both proteins induce cell fusion in a variety of cell types of avian or mammalian origin indicating the general utility of these proteins to induce membrane fusion.

While the invention has been described in detail with reference to certain preferred embodiments thereof, it will be understood that modifications and variations are within the spirit and scope of that which is described and claimed.

SUMMARY OF SEQUENCES

SEQ ID NO:1 is a cDNA nucleotide sequence of the S1 genome segment of reptilian reovirus (RRV). The open reading frame encoding p14 is shown.

SEQ ID NO:2 is the deduced amino acid sequence of the p14 protein encoded by SEQ ID NO:1.

SEQ ID NO:3 is a cDNA nucleotide sequence of the S1 genome segment of reptilian reovirus (RRV). The open reading frame encoding the sigma C protein is shown.

SEQ ID NO:4 is the deduced amino acid sequence of the sigma C protein encoded by SEQ ID NO:1 or 3.

SEQ ID NO:5 is a cDNA nucleotide sequence of genome segment 7 of aquareovirus (AQV). The open reading frame encoding p14 is shown.

SEQ ID NO:6 is the deduced amino acid sequence of the p16 protein encoded by SEQ ID NO:5. Note that the initiator codon is one of the first 17 codons; its precise position has not been determined.

SEQ ID NO:7 is a cDNA nucleotide sequence of genome segment 7 of aquareovirus (AQV). The open reading frame encoding the NS28 protein is shown.

SEQ ID NO: 8 is the deduced amino acid sequence of the NS28 protein encoded by SEQ ID NO:5 or 7.

I claim:

1. An isolated protein comprising the amino acid sequence of SEQ ID NO:2.

* * * * *